(12) United States Patent
De Graaff et al.

(10) Patent No.: US 6,300,112 B1
(45) Date of Patent: Oct. 9, 2001

(54) β-XYLOSIDASE, NUCLEOTIDE SEQUENCE ENCODING IT, AND USE THEREOF

(75) Inventors: Leendert Hendrik De Graaff, Oosterbeek; Noël Nicolaas Maria Elisabeth Van Peij, Wageningen; Henriëtta Catharina Van Den Broeck, Bennekom; Jacob Visser, Wageningen, all of (NL)

(73) Assignee: Danisco Ingredients A.S (Danisco A/S), Brabrand (DK)

(*) Notice: Subject to any disclaimer, the term of this patent is extended or adjusted under 35 U.S.C. 154(b) by 0 days.

(21) Appl. No.: 08/981,446

(22) PCT Filed: Jun. 24, 1996

(86) PCT No.: PCT/NL96/00258
§ 371 Date: Dec. 22, 1997
§ 102(e) Date: Dec. 22, 1997

(87) PCT Pub. No.: WO97/00964
PCT Pub. Date: Jan. 9, 1997

(30) Foreign Application Priority Data

Jun. 23, 1995  (EP) .................................................. 95201707

(51) Int. Cl.[7] .............................. C12N 9/14; C12N 5/02; C12N 15/63; C12P 21/06
(52) U.S. Cl. ...................... 435/195; 435/320.1; 435/325; 435/69.1; 536/23.2; 536/471
(58) Field of Search ................................ 435/195, 320.1, 435/325, 69.1; 536/23.2, 471

(56) References Cited

FOREIGN PATENT DOCUMENTS 0 463 706 A1   1/1992   (EP).

OTHER PUBLICATIONS van Peij, N. et al., Eur. J. Biochem., vol. 245, pp. 164–173, Apr. 1, 1997.*

Database Strand embl: emest1:AT05820, AC=N96058, Apr. 19, 1996 XP002016326.

Plant Physiol., vol. 106, No. 4, Dec. 1994, pp. 1241–1255, Newman: "Gene Galore: a summary of methods for accessing results from large–scale partial sequencing of anonymous Arabidopsis cDNA clones".

J. Applied Biochem., vol. 5, 1983, pp. 300–312, XP002016322 Rodionova et al.: Beta–xylosidase from Aspergillus niger15 : purification and properties.

Suid Afrikaanse Tydskrif vir Natuurwetenskap en Tegnologie, vol. 13, No. 3, Sep. 1994, pp. 66–80, XP002016323 Pretorius et al.: "Die genetiese manipulasie van die gis Saccharomyces cerevisiae vir die moonlijke omskakeling van polisakkariedryke landbougewassw en nywerheidsafval na enkelselprotein en brandstofetanol".

Eur. J. Biochem., vol. 138, No. 2, 1984, pp. 267–273, XP002016324 Panbangred et al.: "Isolation of two Beta–xylosidase genes of *Bacillus pumilus* and comparison of their gene products".

Mol. Microbio., vol. 12, No. 3, 1994, pp. 479–490, XP002016325 De Graaff et al.: "Regulation of the xylanase–encoding xlnA gene *Aspergillus tubigensis*".

* cited by examiner

Primary Examiner—Ponnathapu Achutamurthy
Assistant Examiner—Peter P. Tung
(74) Attorney, Agent, or Firm—Sughrue, Mion, Zinn, Macpeak & Seas, PLLC

(57) ABSTRACT

A nucleotide sequence is provided which encodes a peptide having β-xylosidase activity and exhibits at least 30% amino acid identity with the amino acid sequence shown in SEQ ID NO. 1 and described in SEQ ID NO. 3 or hybridises under stringent conditions with a nucleotide sequence shown in SEQ ID NO. 1, or a part thereof having at least 15 nucleotides encoding an amino acid sequence shown in SEQ ID NO. 1 and described in SEQ ID NO. 3. Also provided is a peptide having β-xylosidase activity and exhibiting at least 30% amino acid identity with the amino acid sequence shown in SEQ ID NO. 1 and described in SEQ ID NO. 3 or a part thereof having at least 8 amino acids shown in SEQ ID NO. 1 and described in SEQ ID NO. 3.

4 Claims, 5 Drawing Sheets

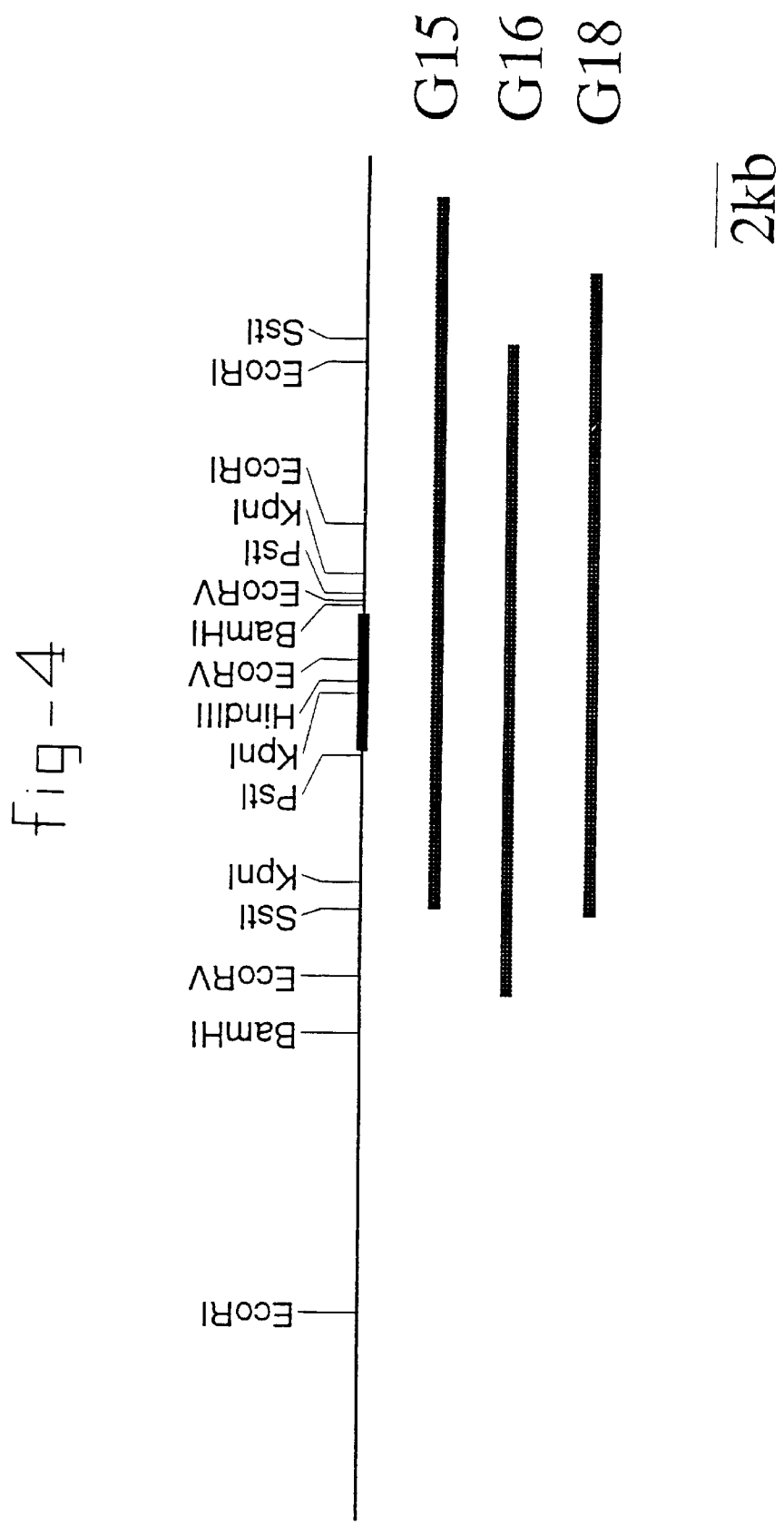

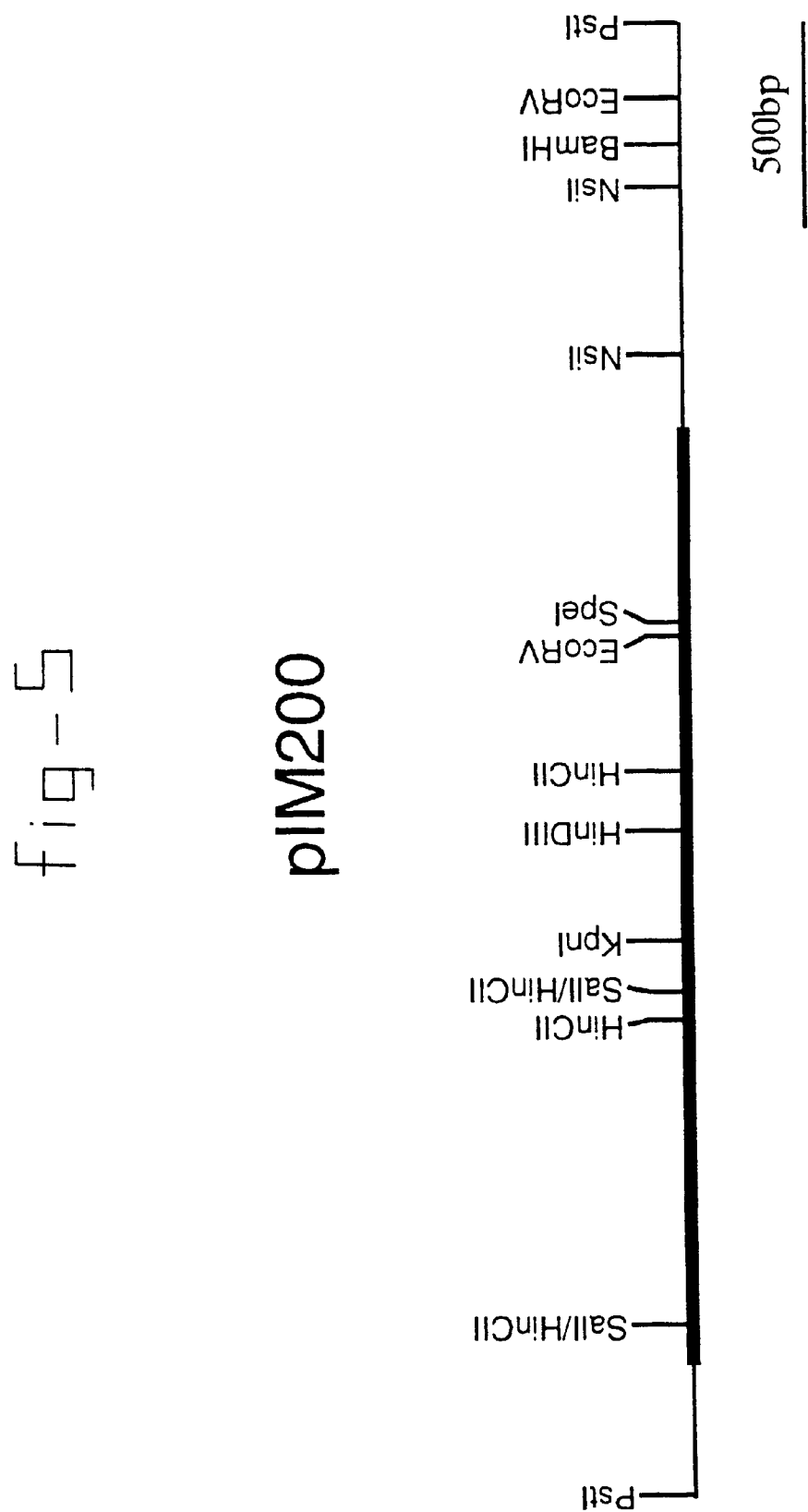

β-XYLOSIDASE, NUCLEOTIDE SEQUENCE ENCODING IT, AND USE THEREOF

Figure 1:
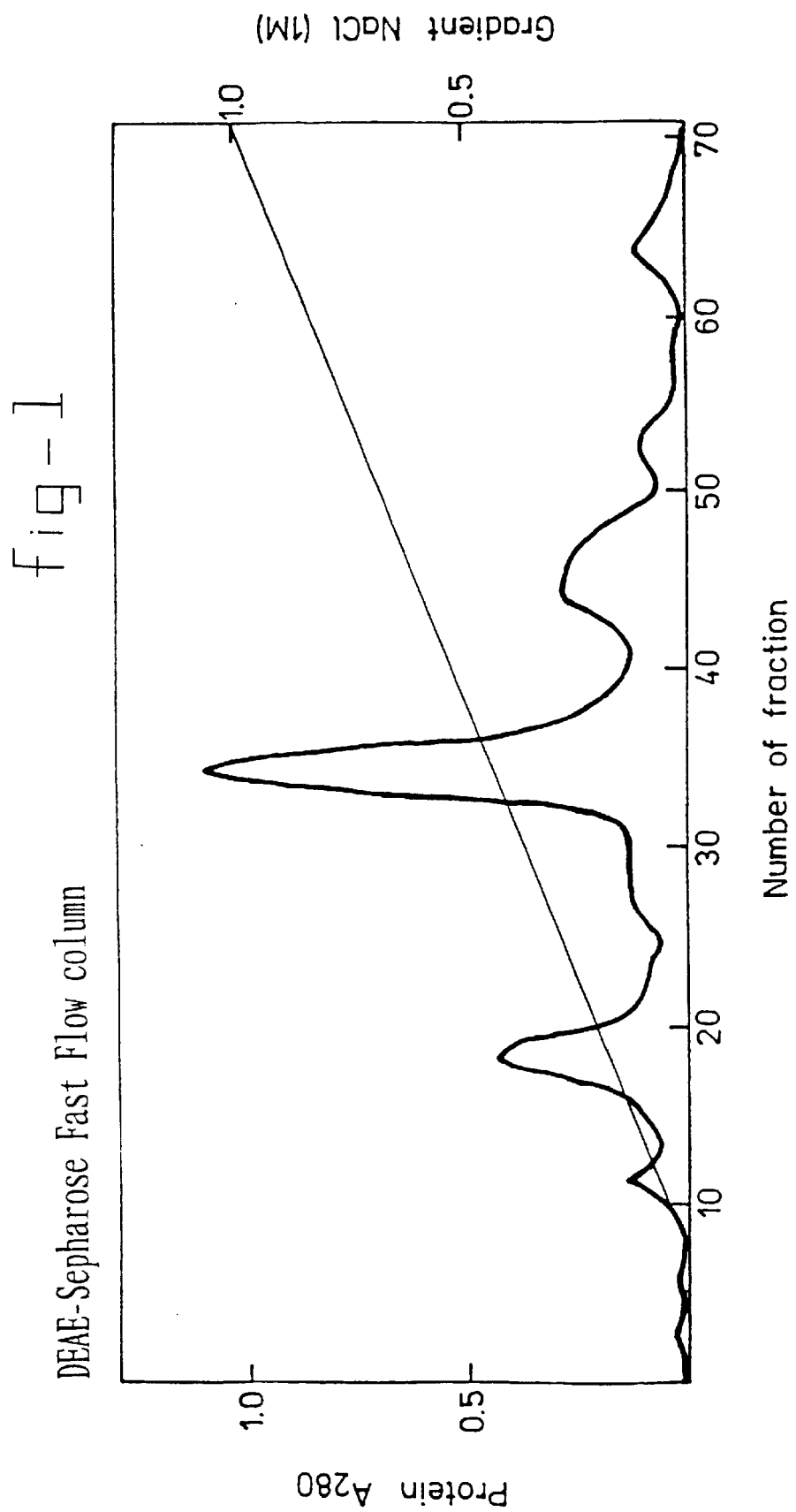

The present invention relates to a novel peptide having β-xylosidase activity, to a nucleotide sequence encoding such a peptide, and to the use of such a β-xylosidase-like peptide.

BACKGROUND

Beta-xylosidase (1,4-β-D-xylan-xylohydrolase; EC 3.2.1.37) is one of the xylanolytic enzymes. Xylans are a major constituent of the cell walls of plants, and are second only to cellulose. They are abundantly found in most land plants, especially in agricultural by-products such as straw, wheat-bran, corn cobs, cotton seed, etc. Xylan is a complex polymer consisting of a β-1,4-linked xylose polymer with arabino-furanose, glucuronic acid, methylglucuronic acid and acetyl side-groups. Endoxylanase (EC 3.2.1.8) randomly cleaves the β-1,4-bonds in the xylan backbone to yield oligosaccharides, xylobiose and xylose. Beta-xylosidase cleaves terminal xylose units from the non-reducing end of the xylose oligomers resulting from endoxylanase activity. α-Glucuronidase cleaves glucuronic acid side groups from backbone xylose units, whereas α-L-arabinofuranosidases (EC 3.2.1.55) cleave arabinose units from the xylan backbone and acetylesterases (EC 3.1.1.6) remove the acetyl side-groups.

Beta-xylosidase is also effective in transglycosylation reactions wherein monosaccharide units or alcohols are attached to or cleaved from xylose units. Beta-xylosidase is rate-limiting in xylan hydrolysis (Dekker 1983, Poutanen and Puls 1988).

The hydrolysing and transglycosylating reactions of β-xylosidases are economically important for the break-down and utilisation of agricultural waste material e.g. in the production of xylose, xylose oligomers and xylitol, which are useful as sweeteners in foodstuffs, candies and medicaments, especially as a sugar substitute. Also, the enzyme or its products can be used as bread improvers and in the beer brewing industry.

Beta-xylosidases have been isolated from various sources including bacteria and fungi. For example, the purification of β-xylosidase from *Aspergillus niger* was reported by Rodionova et al. (1983); the molecular weight was reported to be 253,000 on the basis of gel filtration and 122,000 on the basis of SDS electrophoresis, whereas its isoelectric point was at pH 4.9.

Three endoxylanases and one β-xylosidase were isolated from *Aspergillus awamori* by Kormelink et al. (1993); the β-xylosidase had a molecular weight of 110,000, a pH optimum of 6.5 and a temperature optimum of 70° C.

Beta-D-xylosidase from rumen fungus *Neocallirnastix frontalis* was reported by Garcia-Campayo and Wood (1993) and had an apparent molecular weight (gel filtration) of 150,000, a pH optimum of 6.4 and a temperature optimum of 37° C. Utt et al (1991) report the sequencing of the xylB of the ruminal bacterium *Butyrivibrio fibrisolvens* encoding both β-xylosidase and α-arabinofuranosidase activities.

Known β-xylosidases have activity patterns that do not always correspond to the industrial needs. In particular it is often desirable that the enzyme has a high xylosidase specificity and low specificities for other substrates, such as glucosides and galactosides. Especially fungal β-xylosidases are highly advantageous for their activity levels and specificity patterns.

In order to be able to provide β-xylosidase-like enzymes having the desired activity patterns from the desired production organisms, sequence information of the β-xylosidase gene should be available. Up to now however, no sequence information on fungal β-xylosidases has been reported.

DESCRIPTION OF THE INVENTION

A novel β-xylosidase has now been found and its amino acid sequence as well as its encoding nucleotide sequence have been determined. The protein is denoted herein as xylD, whereas the encoding gene is denoted as xlnD. The primary structure of the novel β-xylosidase appears to be different form known β-xylosidase-like enzymes. Also, its activity pattern is different form known β-xylosidase-like enzymes, and its xylosidase activity is about two times higher than that of the β-xylosidase reported by Rodionova et al (supra).

Accordingly, the invention relates to a nucleotide sequence encoding a peptide having β-xylosidase activity and exhibiting at least 30% amino acid homology with the amino acid sequence shown in SEQ ID NO. 1 and described in SEQ ID NO. 3 or hybridising under stringent conditions with a nucleotide sequence shown in SEQ ID NO. 1, or a part thereof having at least 15, preferably at least 21, more preferably at least 24 or even at least 30 nucleotides encoding an amino acid sequence shown in SEQ ID NO. 1. By amino acid homology is meant here amino acid identity in the primary structure. Amino acid similarity is usually higher than the figures given for identity.

In this context, heterologous hybridisation conditions are as follows: hybridisation in 6×SSC (20×SSC per 1000 ml: 175.3 g NaCl, 107.1 g sodium citrate.-5H$_2$O, pH 7.0), 0.1% SDS, 0.05% sodium pyrophosphate, 5* Denhardt's solution (100×Denhardt's solution per 500 ml: 10 g Ficoll-400, 10 g polyvinylpyrrolidone, 10 g Bovine Serum Albumin (Pentax Fraction V)) and 20 μg/ml denatured herring sperm DNA at 56° C. for 18–24 hrs followed by two 30 min. washes in 5×SSC, 0.1 % SDS at 56° C. and two 30 min. washes in 2×SSC, 0.1% SDS at 56° C.

The nucleotide sequence of the invention encodes a peptide having substantial β-xylosidase activity, i.e. it has β-xylosidase activity as its predominant enzymic activity, and thus may be used for the production of β-xylosidases or mutants thereof. The coding sequences may contain mutations (insertions, deletions or both) which serve to modify the structure and/or the activity of the expression product. For an active expression product, the minimum identity and/or the hybridisation characteristic as defined above should preferably be maintained. The nucleotide sequence may also correspond to regulating or signal sequences of β-xylosidases. For these uses, the nucleotide sequence comprises substantially the encoding or regulating sequences of the β-xylosidase. On the other hand, the nucleotide sequence may be used as a primer or probe in detecting β-xylosidase encoding sequences. For these uses, the sequence comprises at least 15, up to e.g. 60, consecutive nucleotides of the sequence of SEQ ID NO. 1.

The invention also relates to an isolated peptide having β-xylosidase activity and exhibiting at least 30% amino acid homology (identity) with the amino acid sequence shown in SEQ ID NO. 1 and described in SEQ ID NO. 3 or a part thereof, said peptide having no β-glucosidase and/or no β-galactosidase activity; essentially no β-glucosidase or β-galactosidase activity means that these activities are less than 2%, in particular less than 1% of the β-xylosidase activity. A peptide exhibiting at least 40%, preferably at least 60%, most preferably at least 75% amino acid identity with the amino acid sequence shown in SEQ ID NO. 1 and described in SEQ ID NO. 3 forms a preferred embodiment of the invention. Also part of the invention are peptides comprising a series of at least 8 contiguous amino acids of the amino acid sequence shown in SEQ ID NO.1. These can be produced by translating a nucleotide sequence as described above. Preferably the peptide has a contiguous series of at least 10, most preferably at least 12 amino acids from the sequence set forth in SEQ ID NO. 1and described in SEQ ID NO. 3.

The peptide according to the invention is especially from fungal origin, in particular from filamentous fungi, e.g. strains from the genera Aspergillus (especially *A. niger, A.niger* var *tubigensis, A. niger* var *awarnori, A. niger* var *kawachii, A. oryzae, A. sydowii, A. japonicus, A. aculeatus, A. ochraceus, A. terreus, A. fumigatus, A. versicolor, A. flavus, A. phoenicis, A. nidulans, A. foetidus* and *A. carbonarius*), Trichoderma (especially *T. reesei, T viride, T. longibrachiatum, T. harzianum, T. kongingii, T. pseudokongii*), Penicillium (*P. wortrnani, P. pinophilum, P. janthinellum, P. citrinum, P. capsulatum, P. oxalicuni, P. verruculosum, P. chrysogenum*), Humicola (*H. thermophilium=Scytalidium thermophilium*) and Fusariuni (*F. oxysporum, F. solani*).

Also, the invention concerns antibodies raised against a peptide as described above e.g. for purifying β-xylosidases and for determining the presence of β-xylosidases. The antibodies can be produced by immunisation with the peptide described above, using hybridoma techniques which are well-known to the skilled person.

Also claimed are expression vectors and plasmids containing the nucleotide sequences described above under the control of a homologous or heterologous promoter.

Furthermore, the invention is concerned with the use of these sequences for the production of β-xylosidases by different hosts under the control of its own, or heterologous regulatory sequences, or for the production of other peptides using the β-xylosidase promoter sequence. The expression vectors and host cells may contain multiple copies of the xylD-encoding sequences (altered or not with respect to SEQ ID NO. 1) and of other genes.

Host organisms may be homologous production strains or alternatively heterologous hosts. Suitable host organisms include fungi, yeasts, bacteria and plants. Examples are Aspergillus species, Trichoderma species, Bacillus species, Kluyveromyces species, Saccharomy,ces species and Fusariuni species. Particularly preferred are *A. niger, A. niger* var. *tubigensis, A. niger* var. *awamori, A. oryzae, A. japonicus, A. carbonarius, A. aculeatus, T. reesei, T. viride, T. harzianunm, F. oxysporum, B. subtilis, B. licheniformis, K. lactis* and *S. cerevisiae*. The host organism is preferably a food-grade organism.

Examples of own control regions and heterologous regulatory regions include fungal constitutive and/or inducible promoters such as the pyruvate kinase promoter (pkiA) and the glyceraldehyde-3-phosphate dehydrogenase (gpd) promoters. Examples of strong yeast promoters are alcohol dehydrogenase, 3-phosphoglycerate kinase and triose phosphate isomerase promoters. Examples of bacterial promoters are α-amylase, spo2 and promoters of extracellular protease genes.

The invention is furthermore concerned with the use of regulatory sequences contained in the 5'-noncoding part of SEQ ID NO.1 (nucleotides 1-854 or a part thereof) for expression of homologous or heterologous genes, e.g. xylanase, amylase, glucanase, oxidoreductases e.g. hexose oxidase, α-glucuronidase, lipase, esterase, ferulic acid esterase, proteases, or human interleukin-6, bovine (pro) chymosin, human lactoferrin, fungal phytase. A signal sequence of xlnD may be used in such constructs, as well as a suitable terminator, e.g. xlnD or trpC.

Further part of the invention is the use of the nucleotide sequence described above in such a manner as to disrupt the β-xylosidase gene of a host organism. To this end a nucleotide sequence containing a mutation which brings about a defunctionalisation of the β-xylosidase gene is introduced in the host cell. The mutation may be a deletion of one or more nucleotides, an insertion of one or more nucleotides, or a combination thereof.

The host cell—whether altered so as to produce or overproduce β-xylosidase or so as not to produce its β-xylosidase—may advantageously express or overexpress other relevant proteins, including enzymes, in particular other xylanolytic enzymes such as endoxylanases, and/or other enzymes such as amylases, glucanases, oxidoreductases such as hexose oxidase, α-glucuronidase, lipases, esterases, ferulic acid esterase and/or proteases. The corresponding genes may be under the control of homologous control regions or under the control region of the β-xylosidase gene contained in the nucleotide sequence described above.

An especially suitable protein to be expressed by the recombinant host cell according to the invention is the activating regulator of the xylanolytic pathway denoted as xylR. The target genes for this regulator comprise the genes xlnA, xlnB, xlnC (all three endoxylanase-encoding genes), xlnD and axeA. Thus, the host cells according to the invention containing the xlnR gene, i.e. capable of expressing xylR or an active equivalent thereof, are effective producers of β-xylosidase—in case they contain the active xlnD gene—or of other xylanolyitc enzymes including endoxylanases, excluding β-xylosidase—in case their xlnD gene has been defunctionalised. The nucleotide sequence of the xlnR gene is set forth in SEQ ID NO.2.

Also comprised by the invention is the use of the enzyme activity of the peptide in transglycosylation reactions of substrates contained in bread doughs and other bakery products, resulting in improved bread characteristics. This includes the use of the β-xylosidase as a bread improver in a manner known per se for enzymic bread improvers.

The β-xylosidases encoded by the present sequences can also be advantageously used for the production of xylose and xylose oligomers from wood and plant wastes and spent paper pulp, which xylose and oligomers are suitable as sweeteners. They can also be reduced to xylitol, which is also an effective bulk sweetener.

The host cells according to the invention, wherein the β-xylosidase gene has been disrupted, can be used e.g. in the production of enzymes and enzyme preparations e.g. to be added to animal feed. Animals, including poultry and pigs, have a poor metabolism for xylose (Schulte, 1991). Xylose which is absorbed over the gut wall occupies the urinary excretion system land thus xylose uptake is energetically dis-advantageous to the animal. Moreover, a high intake of xylose is known to cause cataracts, diarrhoea and anorexia. On the other hand xylose and xylo-oligomers can be fermented to short chain fatty acids, which is an energetic asset. Therefore hemicellulose-degrading enzymes in feed should produce xylo-oligomers and no xylose monomers, and thus the enzymes should have endoxylanase activity and no, or a reduced level of, β-xylosidase activity. Thus the inventions also pertains to the use of host cells, such as fungi, bacteria, yeasts and plants, having a defunctionalised β-xylosidase gene but being capable of effectively producing endoxylanase and optionally other, especially xylanolytic, enzymes, for the production of enzyme preparations free of β-xylosidase. The invention also comprises such xylanolytic enzyme preparations lacking β-xylosidase activity.

The β-xylosidase encoded by the nucleotide sequence of SEQ ID NO. 1 differs greatly from the β-xylosidase of *A. niger* reported by Rodionova et al. (1993), as is shown in table A.

TABLE A

Activity and inhibition of β-xylosidases of the invention (X-I and X-II), compared to the β-xylosidase according to Rodionova et al. (1983)

| substrate activity (U/mg) | X-I invention | X-II invention | β-xyl (Rodionova) |
|---|---|---|---|
| p-nitrophenyl-β-D-xylopyranoside | 60.2 | 60.9 | 35.2 |
| p-nitrophenyl-β-D-glucopyranoside | 0.2 | 0.3 | 7.9 |
| p-nitrophenyl-β-D-galactopyranoside | 0.0 | 0.0 | 0.6 |
| p-nitrophenyl-α-L-arabinofuranoside | 2.8 | 3.4 | 5.8 |
| inhibition $K_i$ (mM xylose) | 9.8 | 13.2 | 2.9 |

Table A summarises the specificity pattern of two β-xylosidases X-I and X-II of the invention—presumably differing only in their glycosylation pattern, not in their amino acid sequence—and of the β-xylosidase reported by Rodionova et al., and their inhibition by xylose. The amino acid composition of these β-xylosidases is given in table B.

TABLE B

Amino acid composition of β-xylosidase according to SEQ ID NO. 1, compared to the β-xylosidase according to Rodionova et al.

| Amino acid | number | mole % | mole % (Rodionova) |
|---|---|---|---|
| Ala | 86 | 11.1 | 8.2 |
| Arg | 27 | 3.5 | 2.1 |
| Asn + Asp | 95 | 12.2 | 5.6 |
| Cys | 7 | 0.9 | 1.1 |
| Gln + Glu | 74 | 9.5 | 12.4 |
| Gly | 63 | 8.0 | 11.3 |
| His | 13 | 1.7 | 1.4 |
| Ile | 39 | 5.0 | 4.8 |
| Leu | 69 | 8.9 | 8.8 |
| Lys | 24 | 3.1 | 2.9 |
| Met | 6 | 0.8 | 3.3 |
| Phe | 24 | 3.1 | 2.9 |
| Pro | 39 | 5.0 | 8.6 |
| Ser | 53 | 6.8 | 8.7 |
| Thr | 58 | 7.5 | 7.0 |
| Trp | 15 | 2.0 | 2.6 |
| Tyr | 41 | 5.3 | 3.4 |
| Val | 45 | 5.8 | 6.1 |

EXAMPLE 1

Purification of *A. niger* β-xylosidase

Mutant strain *A. niger* NW147, a depressed derivative of strain NW205::130#2 (cspA1, pyrA6, nicA1, argB13, ::pIM130) constructed as described in the copending PCT application filed 96.06.24 (as well as in EP 95201707.7 and EP 95202346.3) was grown in Aspergillus minimal medium (MM) (contains per litre: 6.0 g $NaNO_3$, 1.5 g $KH_2PO_4$, 0.5 g $MgSO_4.7H_2O$, 0.5 g KCl, Carbon source as indicated, pH 6.0 and 1 ml Vishniac solution (Vishniac, W. and Santer, M., 1957) (contains per litre 10 g EDTA, 4.4 g $ZnSO_4.7H_2O$, 1.0 g $MnCl_2.4H_2O$, 0.32 g $CoCl_2.6H_2O$, 0.32 g $CuSO_4.5H_2O$, 0.22 g $(NH_4)_6Mo_7O_{24}.4H_2O$, 1.47 g $CaCl_2.2H_2O$, 1.0 g $FeSO_4.7H_2O$, pH 4.0) supplemented with 1.5 % crude Wheat arabinoxylan, 10 mM L-arginine, 10 μM nicotinamide. This medium was inoculated with $1*10^6$ spores per ml and mycelium was grown for 96 hours at 30° C. and 250 rpm in an orbital New Brunswick shaker. The culture filtrate was collected after filtration of the mycelium on Myracloth (nylon gauze) using a Buchner funnel and mild suction. The pH of the culture filtrate was adjusted to pH 6.0 with 0.1 M NaOH after which the culture filtrate was diluted by the addition of 2 volumes of Millipore water.

Figure 2:
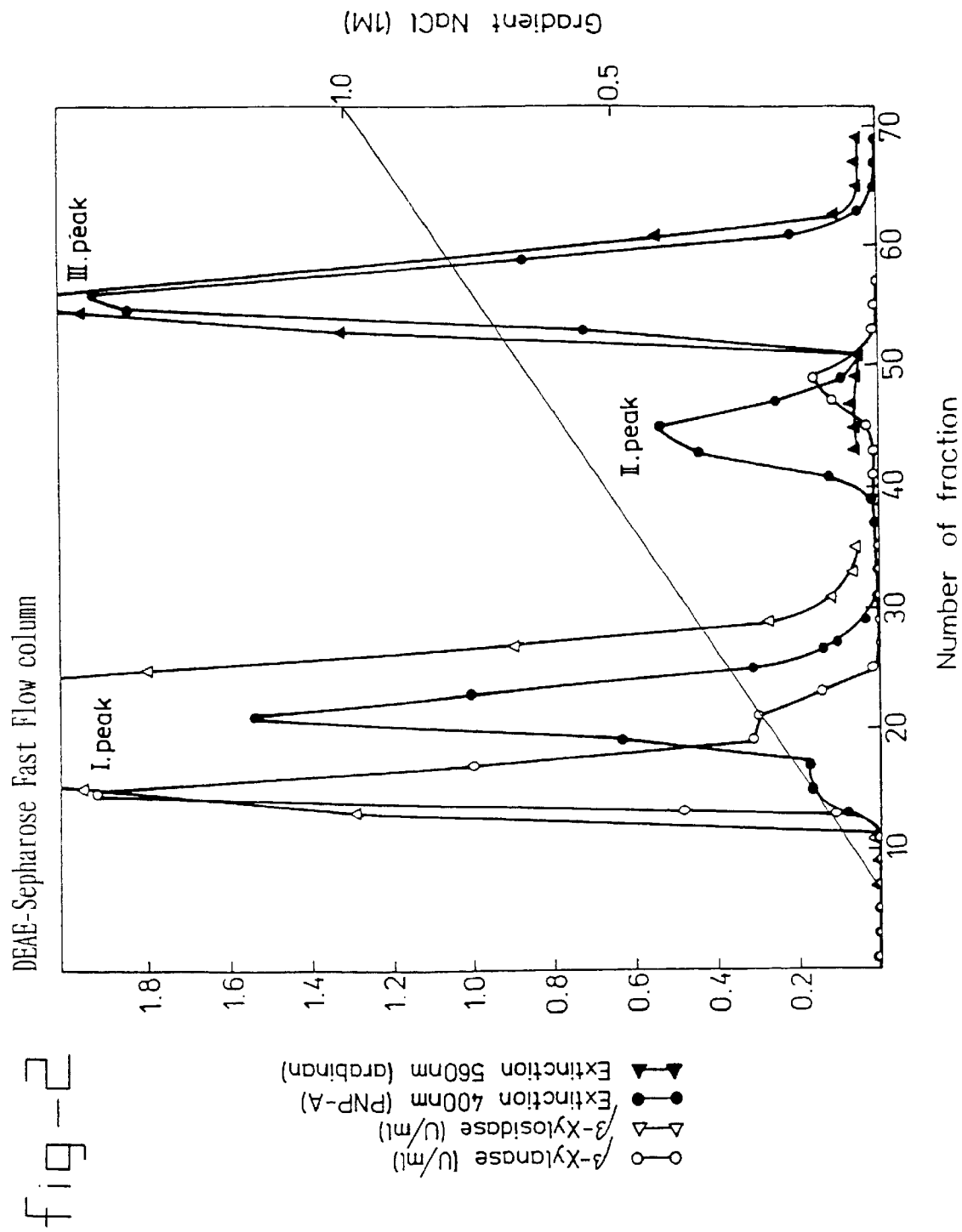
Figure 3:
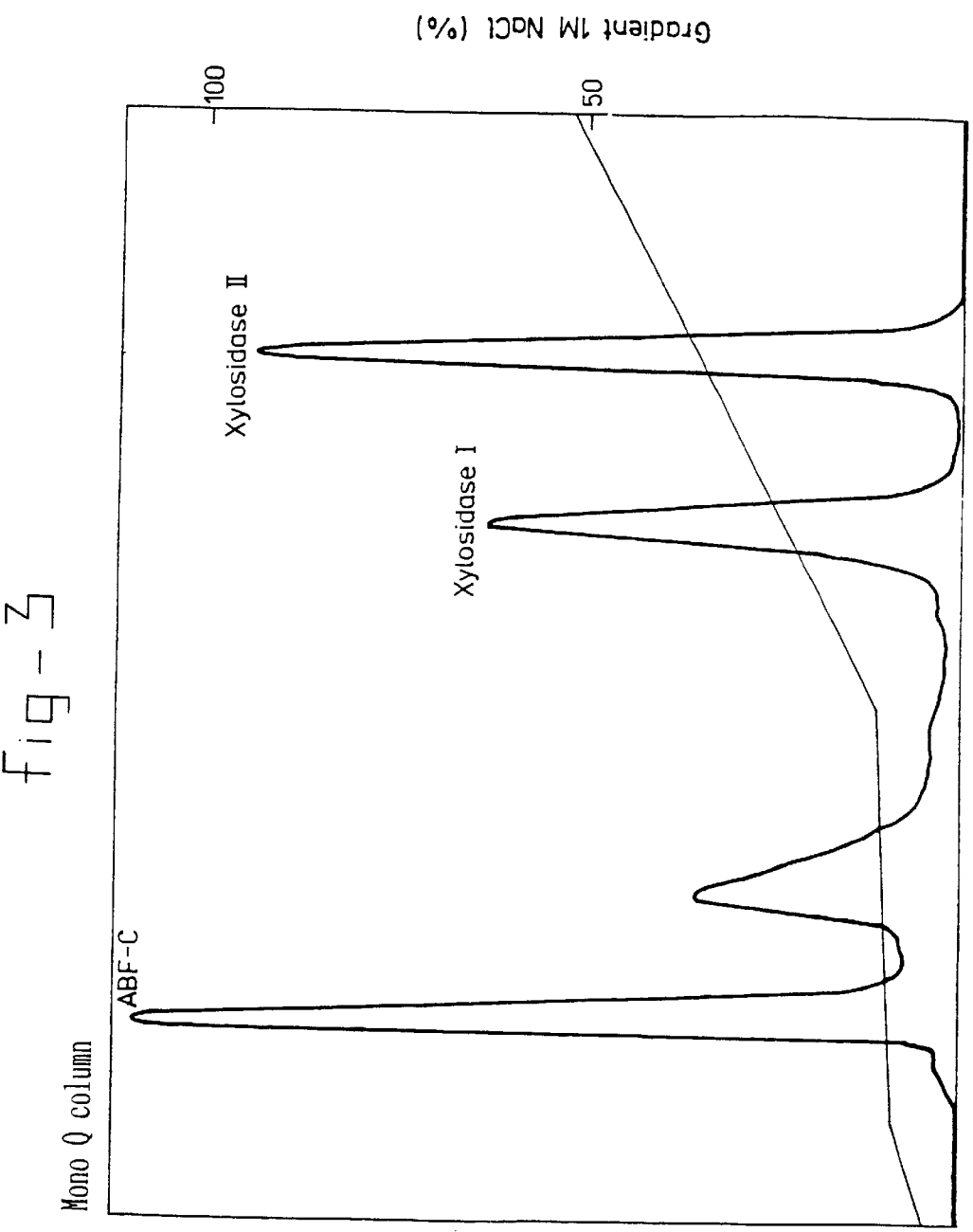

DEAE-Sephadex A-50 was equilibrated in 50 mM sodium acetate buffer pH 5.0 and was added to the culture filtrate. After 30–60 minutes of stirring at 4° C., the DEAE-Sephadex together with the culture filtrate were passed through a funnel with a glass filter holder and the DEAE-Sephadex A-50 was transferred to a column. This column was first eluted with 50 mM sodium acetate buffer pH 5.0, then with 50 mM sodium acetate buffer pH 5.0+0.5 M NaCl. Fractions containing β-xylosidase activity, as was detected using the chromogenic substrate 4-methylumbelliferyl-β-D-xyloside (detects β-xylosidases and endo-xylanases) (Sigma #M7008), were pooled and desalted by dialysis against Millipore water and subsequently dialysed against 20 mM piperazine-HCl buffer pH 5.0. After dialysis the sample was loaded on a DEAE-Sepharose Fast Flow column. This column was first eluted with 3 volumes 20 mM piperazine-HCl buffer pH 5.0 and then with a linear gradient of 0.5 M NaCl in 20 mM piperazine-HCl buffer pH 5.0. Detection of the eluted protein was performed by continuous measurement of the UV absorption at 280 nm (FIG. 1). Fractions of 10 ml were collected which were assayed for activity of β-xylosidase on para-nitro-phenyl-β-D-xylopyranoside (PNP-X) (Sigma #N2132). The β-xylosidase was found in fractions 11–27, which were pooled and subsequently dialysed against 20 mM piperazine-HCl buffer pH 6.0 (FIG. 2). 5 ml of the dialysed sample was applied on a Mono Q HR 5/5 column (Pharmacia). Protein was eluted using 59 ml of a linear gradient of 1 M NaCl in 20 mM piperazine-HCl buffer pH 6.0. Detection of the eluted protein was performed by continuous measurement of the UV absorption at 280 nm (FIG. 3). Two peaks containing β-xylosidase activity were found; β-xylosidase I was eluting at 0.19 M NaCl, while peak II eluted at 0.29 M NaCl. SDS-PAGE of both peak fractions revealed that the fractions corresponding with both peaks each contained a single protein band, both having the same apparent molecular weight of 110 kDa. The specific activity of both β-xylosidase I and II towards the artificial substrate PNP-X was determined as described by Rodionova et al., 1983, to be respectively 60.2 and 60.9 U/mg protein. In addition the activity against PNP-β-D-glucopyranoside (Sigma #N7006) was determined to be 0.2 and 0.3 U/mg, against PNP-β-D-galactopyranoside (Sigma #N1252) 0.0 and 0.0 U/mg and against PNP-β-L-arabinofuranoside (Sigma #N3641) 2.8 and 3.4 U/mg respectively for β-xylosidase I and II.

EXAMPLE 2

Construction of a cDNA Expression Library

*A. niger* NW147 was cultivated for 69 and 81 hr on MM containing 2% wheat arabinoxylan after which the mycelium was harvested by filtration and then washed with sterile saline. The mycelium was subsequently frozen in liquid nitrogen after which it was powdered using a Microdismembrator (Braun). Total RNA was isolated from the mycelial powder in accordance with the guanidium thiocyanate/CsCl protocol described in Sambrook et al. (1989), except that the RNA was centrifuged twice using a CsCl gradient. Poly A$^+$ mRNA was isolated from 5 mg of total RNA by oligo(dT)-cellulose chromatography (Aviv and Leder, 1972, Sambrook et al., 1989) with the following modifications: SDS is omitted from all solutions and the loading buffer was supplemented with 9% (v/v) dimethylsulfoxide.

cDNA was synthesised from 7 μg poly A$^+$ mRNA and ligated into bacteriophage lambda Uni-ZAP XR using the ZAP™-cDNA synthesis kit (Stratagene) according to the manufacturer's instructions. After ligation of the cDNA into Uni-ZAP XR vector-arms, the phage DNA was packaged using Packagene™ extract (Promega) according to the manufacturer's instructions. Ligation of 120 ng cDNA in 1.2 μg vector arms and subsequent packaging of the reaction mixture resulted in a primary library consisting of 3.5*10$^4$ recombinant phages. This primary library was amplified using *E. coli* XL1-Blue MRF' (Stratagene), titrated and stored at 4° C.

EXAMPLE 3

Preparation of Antibodies Against β-xylosidase

250 μg of both β-xylosidase I and II was dialysed against 1 mM phosphate buffer pH 7.0 and freeze-dried. The protein was resuspended in 100 μl sterile PBS (0.136 M NaCl; 2.7 mM KCl; 8 mM Na$_2$HPO$_4$; 1.75 mM KH$_2$PO$_4$; pH 7.4). To this protein mixture, 100 μl of Freunds' complete adjuvant was added and vortexed for 30 minutes to obtain a stable emulsion. For both proteins this mixture was injected into a mouse subcutaneously. In week 4 a booster was given by injecting 25 μg β-xylosidase in 100 μl sterile PBS to which 100 μl of Freunds' incomplete adjuvant was added. The mice were bled in week 7 and the serum tested. In week 13 the mice was given a second booster of 25 μg followed by a bleeding in week 14. This procedure of boosters with nn interval of 6 weeks followed by a bleeding may be repeated several times.

The collected blood was incubated for 30 minutes at 37° C. and subsequently stored at 4° C. for 16 hours. After centrifugation at 5000 rpm in a Sorvall High speed centrifuge the serum was collected and stored at –20° C.

EXAMPLE 4

Immunoscreening of the *A. niger* NW147 cDNA Library with Antibodies Against β-xylosidase II To screen the *A. niger* NW147 cDNA library, constructed as described in Example 2, for β-xylosidase expressing cDNA clones 5*10$^3$ pfu per plate were plated in NZYCM top-agarose containing 0.7% agarose on 85-mm-diameter NZYCM (1.5% agar) plates as described (Maniatis et al., 1982, pp. 64), using *E. coli* BB4 (Stratagene) as plating bacteria. Screening of the cDNA expression library obtained was basically performed as described by Young and Davies (1983). In short, 5000 pfu of the amplified stock were plated on NZYCM medium using *E. coli* BB4 cells as a host in 0.7 % top-agarose. Plates were incubated for 5 hrs at 37° C. after which they were covered with nitrocellulose filters which were previously soaked in 10 mM IPTO and air-dried. Plates were then further incubated for 6 hrs at 37° C. Plates were cooled to 4° C., the position of the filters on the plates was marked before they are removed. The filters were incubated for 15 min in 0.5 M NaCl, 0.05 % Tween. 20 (Biorad), 20 mM Tris/HCl pH 7.5 with gentle shaking, this was repeated once. The bacterial debris was removed by gentle scrubbing with gloved hands. Phages expressing a fusion protein containing a part of the β-xylosidase protein were identified by probing the filters with anti β-xylosidase II antiserum and subsequent detection using an alkaline phosphatase conjugate, according to the procedure described for Western blots in the appropriate Biorad manual. In two experiments 5*10$^3$ and 5*10$^4$ pfu of the amplified library were screened for expression of β-xylosidase cDNA; 4 positives were found. Each positive plaque was removed from the plate using a Pasteur pipette and the phages were eluted from the agar plug in 1 ml of SM buffer containing 20 μl chloroform, as described in Maniatis et al. (1982). The phages obtained were purified by repeating the procedure described above using filter replicas from plates containing 50–100 plaques of the isolated phages.

EXAMPLE 5

Analysis of β-xylosidase Expressing cDNA Clones

The cDNA clones expressing β-xylosidase were converted to Bluescript phagemids using super infection with the filamentous helper phage ExAssist™, which is included in the ZAP™-cDNA synthesis kit from Stratagene, according to the manufacturer's instructions.

The phagemid DNA was subsequently isolated as described in Sambrook et al. (1989). The isolated DNA of the 4 cDNA clones was subjected to restriction analysis using the restriction enzymes EcoRI and XhoI. The DNA was digested for 2 hours at 37° C. in a reaction mixture composed of the following solutions; 2 μl (≈1 μg) DNA solution; 2 μl of the appropriate 10*React buffer (Life Technologies); 10 U of each restriction enzyme (Life Technologies) and sterile distilled water to give a final volume of 20 μl. After addition of 4 μl DNA loading buffer the samples were loaded on a 0.7% TAE-agarose gel. The DNA fragments were separated by electrophoresis at 80 V for 1.5 hours. The restriction analysis revealed that the cDNA clones had inserts of different sizes of respectively 1.4, 1.5, 2.4 and 2.5 kb. The nucleotide sequences of a part of each of these cDNA's were determined by the dideoxy-nucleotide chain-termination procedure (Sanger et al., 1977) using the Pharmacia T7 DNA polymerase sequencing kit. The sequences obtained revealed that these cDNA's correspond all four to the same gene.

EXAMPLE 6

Screening of the *A. niger* Genomic Library for the β-xylosidase Encoding xlnD Gene and Isolation of the Gene For the screening of the *A. niger* N400 genomic library, constructed as described by Harmsen et al., 1990, for the xlnD gene 3×10$^3$ pfu per plate were plated in NZYCM top-agarose containing 0.7% agarose on five 85-mm-diameter NZYCM (1.5% agar) plates as described (Maniatis et al., 1982) using *E. coli* LE392 as plating bacteria. After overnight incubation of the plates at 37° C. two replicas of each plate were made on HybondN$^+$ filters (Amersham) as described in Maniatis et al. (1982). After wetting the filters in 3×SSC the filters were washed for 60 min. at room temperature in 3×SSC. Hybridisation using a $^{32}$P-labelled 2.5 kb EcoRI/XhoI fragment of cDNA clone #4, prepared as described by Sambrook et al., 1989, was done according the following procedure (Sambrook et al., 1989); prehybridisation in 6×SSC (20×SSC per 1000 ml: 175.3 g NaCl, 107.1 g sodium citrate.5.5 $H_2O$, pH 7.0), 0.1% SDS, 0.05% sodium pyrophosphate, 5* Denhardt's solution (100× Denhardt's solution per 500 ml : 10 g Ficoll-400, 10 g polyvinylpyrrolidone, 10 g Bovine Serum Albumin (Pentax Fraction V)) and 20 μg/ml denatured herring sperm DNA at 68° C. for 3–5 hrs and hybridisation in an identical buffer, which contained the denatured radiolabelled probe at 68° C. for 15–18 hrs, followed by two washes in 2×SSC, 0.1 % SDS at 68° C. and two washes in 0.2×SSC, 0.1% SDS at 68° C. The membrane was covered with Saran wrap and autoradiographed overnight at −70° C. using Konica X-ray films and Kodak X-Omatic cassettes with regular intensifying screens.

This screening resulted in about 50 positive phages, of which ten were purified. Each positive plaque was picked from the plate using a Pasteur pipette and the phages were eluted from the agar plug in 1 ml of SM buffer containing 20 μl chloroform, as described in Maniatis et al. (1982). The phages obtained were purified by repeating the procedure described above using filter replicas from plates containing 50–100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 h. at 4° C. with intermittent shaking. After collection of the supernatant using a pipette, the bacteria were removed from the solution by centrifugation at 4,000×g for 10 min. at 4° C. To the supernatant 0.3% chloroform was added and the number of pfu was determined. These phage stocks contain approximately $10^9$ pfu/ml.

DNA of four selected phages G15–G18, isolated as described in Sambrook et al 1989. was analyzed by Southern analysis. The DNA was digested for 5 h. at 37° C. in a reaction mixture composed of the following solutions; 5 μl (≈1 μg) DNA solution; 2 μl of the appropriate 10×React buffer (Life Technologies); 10 U Restriction enzyme (Life Technologies) and sterile distilled water to give a final volume of 20 μl. The samples were incubated for 10 min. at 65° C. and rapidly cooled on ice, before loading on a 0.6% agarose gel in 1*TAE buffer. The DNA fragments were separated by electrophoresis at 25 V for 15–18 h.

After electrophoresis the DNA was transferred and denatured by alkaline vacuum blotting (VacuGene XL, Pharmacia LKB) to nylon membrane (Hybond N, Amserham) as described in the VacuGene XL instruction manual (pp. 25–26) and subsequently prehybridised and hybridized using the labelled 2.5 kb EcoRI/XhoI fragment of cDNA clone#4 and hybridisation conditions as described. The hybridisation pattern was obtained by exposure of Kodak XAR-5 X-ray film for 18 h. at −70° C. using an intensifying screen. In all four clones fragments originating from the same genomic region were found for which a restriction map was constructed (FIG. 4).

Based on the restriction map a 3.6 kb PstI fragment was selected for subcloning. 100 ng pEMBL19 PstI digested fragment was mixed with 250 ng 3.8 kb PstI fragment and 4 μl 5*ligation buffer (composition; 500 mM Tris-HCl, pH 7.6; 100 mM $MgCl_2$; 10 mM ATP; 10 mM dithiothreitol; 25% PEG-6000) and 1 μl (1.2 U/μl) $T_4$ DNA ligase (Life Technologies) was added to this mixture in a final volume of 20 μl. After incubation for 16 h at 14° C. the mixture was diluted to 100 μl with sterile water. 10 μl of the diluted mixture was used to transform E. coli DH5α competent cells, prepared as described by Sambrook et al., 1989. Six of the resulting colonies were grown overnight in LB medium (LB medium per 1000 ml: 10 g trypticase peptone (BBL), 5 g yeast extract (BBL), 10 g NaCl, 0.5 mM Tris-HCl pH 7.5) containing 100 μg/ml ampicillin. From the cultures, plasmid DNA was isolated by the alkaline lysis method as described by Maniatis et al. (1982), which was used in restriction analysis to select a clone harbouring the desired plasmid pIM200. The strain containing the plasmid pIM200 was deposited at the Centraal Bureau voor Schimmelcultures, Baarn, NL, under access number CBS 677.96. Plasmid DNA was isolated on a large scale from 500 ml cultures E. coli DH5α containing pIM200 grown in LB medium containing 100 μg/ml ampicillin (Maniatis et al., 1982). The plasmid was purified by CsCl centrifugation, ethanol precipitated and dissolved in 400 μl TE. The yield was approximately 500 μg. This plasmid was used to construct a detailed restriction map (FIG. 5).

EXAMPLE 7

Transformation of A. niger using the Plasmid pIM200

250 ml of culture medium, which consists of MM supplemented with 2% glucose, 0.5% yeast extract, 0.2% casamino acids (Vitamin free), 2 mM leucine, 10 μM nicotinamide, 10 mM uridine, was inoculated with $1*10^6$ spores per ml of strain NW155 (cspA1, argB13, pyrA6, nicA1, leuA1, prtF28) (derived from NW228, Van den Hombergh et al, 1995) and mycelium was grown for 16–18 hours at 30° C. and 250 rpm in a orbital New Brunswick shaker. The mycelium was harvested on Myracloth (nylon gauze) using a Büchner funnel and mild suction and was washed several times with SP6 (SP6: 0.8% NaCl, 10 mM Na-phosphate buffer pH 6.0). 150 mg Novozyme 234 was dissolved in 20 ml SMC (SMC: 1.33 M sorbitol, 50 mM $CaCl_2$, 20 mM MES buffer, pH 5.8) to which 1 g (wet weight) mycelium was added and which was carefully re-suspended. This suspension was incubated with gentle shaking for 1–2 hours at 30° C., every 30 minutes the mycelium was carefully resuspended and a sample was taken to monitor protoplast formation using a haemocytometer to count the protoplasts. When sufficient protoplasts were present (more then $1*10^8$) these were carefully resuspended and the mycelial debris was removed by filtration over a sterile glasswool plug. The protoplasts were collected by 10 minutes centrifugation at 3000 rpm and 4° C. in a bench centrifuge, the supernatant was removed and the pellet was carefully resuspended in 5 ml STC (STC: 1.33 M Sorbitol, 50 mM $CaCl_2$, 10 mM Tris/HCl, pH 7.5). This wash step was repeated twice and the protoplasts were finally resuspended in STC at a density of $1*10^8$ per ml.

The transformation was performed by adding 20 μg of pIM200 DNA and 5 μg pGW635, containing the A. niger pyrA gene (dissolved in a 10–20 μl TE), to 200 μL of protoplast suspension together with 50 μl of PEG buffer (PEG Buffer: 25% PEG-6000, 50 mM $CaCl_2$, 10 mM Tris/HCl pH 7.2), mixed gently by pipetting up and down a few times, and incubated at room temperature for 20 minutes. After this period 2 ml PEG buffer was added, the solution was mixed gently and incubated at room temperature for another 5 minutes and subsequently 4 ml of STC was added and mixed gently on a vortex mixer. One ml portions of this suspension were then added to 4 ml of 0.95 M sucrose osmotically stabilised top agar and poured on osmotically stabilised plates. As a control A. niger was also transformed using pGW635.

EXAMPLE 8

Analysis of Transformants

The transformants from pIM200 obtained in Example 7 were analyzed phenotypically by plating on MM containing 1% oat spelt xylan and 1 mM 4-methylumbelliferyl-β-D-xyloside. Of the 26 transformants tested, five had an increased fluorescence. These transformants, together with a PYR$^+$ transformant as a reference, were grown on MM containing 1% oat spelt xylan for 20, 27 and 42 hrs, after which the β-xylosidase activity towards PNP-X was measured. The results are summarised in Table C.

An increased level of β-xylosidase activity was found in all five transformants selected, the highest level being more then 30 times the wild-type activity. These results were confirmed by Western blot analysis, using the anti β-xylosidase antibody, prepared as described in Example 3, and the Bio-Rad Immun-blot GAR-AP assay kit following the suppliers instructions.

TABLE C

β-xylosidase activities in *A. niger* transformants activity (mU/ml culture filtrate) after:

|         | 20 hr | 27 hr | 42 hr |
|---------|-------|-------|-------|
| pGW 635 | 15    | 16    | 17    |
| XlsA1   | 82    | 86    | 51    |
| XlsA4   | 90    | 112   | 78    |
| XlsA8   | 211   | 239   | 384   |
| XlsA9   | 63    | 110   | 74    |
| XlsA12  | 96    | 295   | 527   |

EXAMPLE 9

The Primary Structure of the xlnD Gene

9.1: Sequence Analysis of the *A. niger* xlnD Gene

The sequence of the *A. niger* xlnD gene, its promoter/regulation region, the structural part of the gene and the termination region, was determined by subcloning fragments in pEMBL18/19, in combination with the use of specific oligonucleotides as primers in the sequencing reactions.

For nucleotide sequence analysis, restriction fragments were isolated which were then cloned in pEMBL18/19 DNA vectors and digested with the appropriate restriction enzymes. The nucleotide sequences were determined by the dideoxynucleotide chain-termination procedure (Sanger et al., 1977) using the Pharmacia T7 DNA polymerase sequencing kit. Computer analysis was done using the PC/GENE program (Intelligenetics). The sequence determined is given in SEQ ID NO:1.

9.2: Description of the xlnD Gene

The sequence comprising the xlnD structural gene (SEQ ID NO:1) is preceded by a 854 nucleotide long upstream region. A putative TATA box is found at position 787–794. The structural part of the xlnD gene ranges from position 855 till position 3266 and contains no introns, as was certified by sequencing both the cDNA fragment as well as the genomic fragment in pIM200.

The xlnD gene encodes a protein of 804 amino acids. The N-terminal amino acid sequence is preceded by a 26 amino acids long hydrophobic sequence, which presumably corresponds to the signal sequence. The mature β-xylosidase protein is 778 amino acids in length, and has a deduced molecular weight of 84,727 Da.

EXAMPLE 10

Screening of the *A. tubigensis* Genomic Library for the β-xylosidase Encoding xlyD Gene For the screening of the *A. tubigensis* genomic library, constructed as described by De Graaff et al., 1994, for the *A. tubigensis* counterpart, $3 \times 10^3$ pfu per plate were plated in NZYCM top-agarose containing 0.7% agarose on five 85 mm diameter NZYCM (1.5% agar) plates as described in Example 6. Hybridisation using a $^{32}$P-labelled 3.6 kb PstI fragment of pIM200 prepared as described by Sambrook et al., 1989, was done according the following procedure (Sambrook et al., 1989); prehybridisation in 6×SSC, 0.1% SDS, 0.05% sodium pyrophosphate, 5*Denhardt's solution (see Example 6) and 20 μg/ml denatured herring sperm DNA at 65° C. for 3–5 hrs and hybridisation in an identical buffer which contained the denatured radiolabelled probe at 65° C. for 15–18 hrs, followed by two washes in 5×SSC, 0.1% SDS at 65° C. and two washes in 0.2×SSC, 1% SDS at 65° C. The membrane was covered with Saran wrap and autoradiographed overnight at −70° C. using Konica X-ray films and Kodak X-Omatic cassettes with regular intensifying screens.

This screening resulted in about 10 positive phages which were all purified. Each positive plaque was picked from the plate using a Pasteur pipette and the phages were eluted from the agar plug in 1 ml of SM buffer containing 20 μl chloroform, as described in Maniatis et al. (1982). The phages obtained were purified by repeating the procedure described above using filter replicas from plates containing 50–100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 h. at 4° C. with intermittent shaking. After collection of the supematant using a pipette, the bacteria were removed from the solution by centrifugation at 4,000 ×g for 10 min. at 4° C. To the supernatant 0.3% chloroform was added and the number of pfu is determined. These phage stocks contain approximately $10^9$ pfu/ml.

EXAMPLE 11

Disruption of the *A. niger* xlnD Gene

11.1: Construction of the Disruption Plasmids pIM203 and pIM204

The gene disruption plasmids pIM203 and pIM204 were constructed by generating an internal fragment of the xlnD gene by PCR. The fragment was generated using the oligonucleotides derived from the xlnD sequence (SEQ ID NO: 1). Xylos001 was derived from positions 1157 till 1176 and xylos004 was derived from positions 3147 till 3164. The fragment was generated by PCR containing 10 μl 10*reaction buffer (100 mM Tris-HCl, pH 8.3, 500 mM KCl, 15 mM MgCl$_2$, 0.01% gelatine), 16 μl 1.25 mM of each of the four deoxynucleotide triphosphates, 1 ng of the plasmid pIM200 DNA and 1 μg of each of the oligonucleotides in a final volume of 100 μl. This reaction mixture was mixed and 1 μl TAQ polymerase (5 U/μl) (Life Technologies) was added. The DNA was denatured by incubation for 3 min at 92° C. followed by 25 cycli of 1 min 92° C., 1,5 min 52° C. and 1,5 min 72° C. After these 25 cycli the mixture was incubated for 5 min at 72° C. Analysis of the reaction products by agarose electrophoresis revealed a fragment of about 2000 bp, which corresponds to the size expected, based on the sequence of the gene. The resulting fragment was subcloned in the vector pGEM-T (Promega) resulting in the plasmid pIM202. Plasmid pIM203 was constructed by ligation of a SmaI/PstI fragment of pILJ16 (Johnstone et al., 1985), containing the A. nidulans argB gene (Upshall et al., 1986), in the EcoRV/PstI digested pIM202 vector. Plasmid pIM204 was constructed by ligation of the NsiI/XbaI fragment of pIM130 UP 95202346.3), containing the pyrA gene under the control of the UAS of the xlnA promoter of A. tubigensis, in the SpeI/NsiI digested pIM202 vector.

11.2: Disruption of the xlnD Gene in A. niger

The plasmids containing the xlnD internal fragment as well as the argB gene (pIM203) or the pyrA gene (pIM204), as described in Example 11.1, as a selection marker in transformation, were used to disrupt the A. niger xlnD gene. For this A. niger N902 (argB15, cspA1, fwnA1, metB10, pyrA5) was transformed, as described in Example 7, using the plasmids pIM203 and pIM204 selecting for arginine or uridine prototrophy respectively. The resulting transformants were screened for activity on methylumbelliferyl-β-D-xyloside on a 1% xylan plate as described in Example 8. For both groups of transformants twenty were screened. Of these transformants one of each group had a severe decreased level of MUX activity after 24 h of growth. Southern analysis of the selected transformants demonstrated for the pIM203 transformant a multicopy integration at the homologous xlnD locus. In case of the pIM204 transformant a single homologous integration at the xlnD locus had occurred. Analysis for PNP-X activity, as described in Example 8, of these transformants revealed an at least 100-fold decrease in β-xylosidase activity.

11.3: Effect of Overexpression and Inactivation of xlnD Gene on the Expression of Xylanolytic System of A. niger To determine the effect of xlnD expression on the expression of the xylanolytic spectrum, A. niger N902, two xlnD multicopy-transformants in N902 and the xlnD gene disruption strains were grown in liquid culture. This was done in a transfer experiment into 2% oat spelt xylan or 3% D-xylose as a carbon source, after a preculture in 1% fructose for 18 h. Beta-xylosidase activity was determined as PNP-X activity in the culture filtrate. With both C sources a clear overexpression could be seen for the pIM200 transformants against an almost absense of PNP-X activity for both (pIM203 and pIM204) inactivation transformants. The xlnD gene disruption transformants showed an initial decreased level of endo-xylanase expression, which however increased in time finally after 16 hrs resulting in increased activity levels in comparison to the A. niger wild-type, thus resulting in xylanase preparations free of β-xylosidase.

The culture filtrates were subsequently analyzed by HPLC analysis, using a Dionex system and Pulsed Amperometric Detection. For this 1 ml of culture filtrate was boiled immediately after harvesting, to inactivate the xylanolytic enzymes, after which the sample was centrifuged for 10 min. (14.000 rpm at 4° C., Eppendorf centrifuge). The resulting supematant was diluted 5-fold in bidest and 20 µl was analyzed by HPLC using a Dionex CarboPac 100 column. The analysis indicated that, while in the wild-type and in the over-expression transformants only in the initial stage xylose oligomers could be detected in the culture filtrate, in the disruption mutant xylobiose and to a lesser extend xylotriose accumulated in the culture filtrate, thus resulting in a source for xylooligomers, in particular xylobiose and xylotriose.

EXAMPLE 12

Expression of the A. niger xlnD Gene in A. nidulans

The plasmid pIM200 was introduced into A. nidulans by cotransformation of A. nidulans G191 (Balance and Turner, 1985) using the A. niger pyrA gene, located on the plasmid pGW635 as a selective marker and the plasmid pIM200 as the cotransforming plasmid. Protoplasts were prepared as described in Example 7 and the transformation procedure was performed using 1.2 M Sorbitol for osmotic stabilisation, 1 µg pGW635 and 25 µg pIM200. The PYR+ obtained were then screened for xylD expression using the plate assay described in Example 8.

From this screening, five transformants were selected to determine β-xylosidase activity. The A. nidulans wild-type strain and the selected transformants cultivated for 26 h at 37° C. on minimal medium containing either 2% Birchwood xylan (Roth) or 3% D-xylose as an inducing carbon source. After removal of the mycelium, the β-xylosidase activity towards PNP-X in the culture filtrate was determined. The results are summarised in table D. The results show that xylD can be expressed in A. nidulans by using the native expression signals.

TABLE D

| Strain of A. nidulans | Activity on 2% xylan (mU/ml) | Activity on 3% D-xylose (mU/ml) |
| --- | --- | --- |
| WG096 (Wt) | 16 | 0 |
| G191::200–5 | 725 | 48 |
| G191::200–7 | 96 | 11 |
| G191::200–9 | 249 | 40 |
| G191::200–13 | 520 | 33 |
| G191::200–15 | 1525 | 210 |

EXAMPLE 13

Screening Filamentous Fungi for the xlnD Gene

To analyse whether it is possible to isolate the xlnD counterpart from other fungi by heterologous hybridisation, using the 2.5 kb PstI/NsiI fragment of the xlnD gene as a probe, DNA was isolated from the following strains; A. niger N902 (argB15, cspA1, fwnA1, metB10, pyrA5), A. tubigensis NW184 (cspA1, fwnA1, pyrA22), A. nidulans WG096 pabaA1, yA2) of FGSC 187, A. acrileatus NW240 (pyrA3) of CBS 101.43, A. aculeatus NW217 (fwnA1, cspA1, pyrA4, lysA1) of CBS 115.80, A. foetidus (awamori) NW183 (cspA1, fwnA1, pyrA13, lysA1) of CBS 115.52 and Trichoderma reesei QM9414. 1–2 µg DNA was digested with BamHI or with XhoI and subsequently analyzed by Southern analysis. The hybridisation conditions used were; hybridisation in 6×SSC (20×SSC per 1000 ml: 175.3 g NaCl, 107.1 g sodium citrate.5H$_2$O, pH 7.0), 0.1% SDS, 0.05% sodium pyrophosphate, 5*Denhardt's solution (see Example 6) and 20 µg/ml denatured herring sperm DNA at 56° C. for 18–24 hrs followed by two 30 min. washes in 5×SSC, 0.1% SDS at 56° C. and two 30 min. washes in 2×SSC, 0.1% SSC at 56° C. After hybridisation the membrane was covered with Saran wrap and autoradiographed overnight at −70° C. using Konica X-ray films and Kodak X-Omatic cassettes with regular intensifying screens.

As a result hybridising fragments were found for all fungi analysed, very strong hybridisation signals were found in *A. niger, A. tubigensis, A. aculeatus, A. japonicus*, and *A. foetidus*, while strong hybridisation signals were found in *A. nidulans* and *Trichoderma reesei*.

EXAMPLE 14

Effect of xlnR Gene Dosage on the Expression of the *A. niger* Xylanolytic System The strain N902::200-18, harbouring multiple copies (about 6) of the *A. niger* xlnD gene encoding β-xylosidase, was transformed to arginine prototrophy in a co-transformation experiment, as described in Example 11 using 19 μg of the xlnR harbouring plasmid pIM230 and 2μg of the plasmid pIM650 harbouring the *A. nidulans* argB gene (Johnstone et al., 1985). The transformants obtained were screened for increased endo-xylanase expression, on MM plates containing 1% oat spelt xylan. Four colonies, having the fastest and largest halo formation, were selected to determine xlnR copy numbers. For this DNA of these transformants and the recipient strain, was isolated and serial dilutions were spotted onto Hybond N membrane. The copy number was estimated from the signals found after hybridisation, using a radiolabelled 4.5 kb SmaI/XbaI fragment spanning the coding sequence of the xlnR gene. Based on comparison to the recipient strain the xlnR copy number was determined to be 8 in N902::200-18-R14 and 32 in N902::200-18-R16. For both these transformants the effect of the increased gene dosage of xlnR was analysed by Northern analysis after strains were grown in liquid culture. This was done in a transfer experiment into 2% oat spelt xylan as a carbon source, after a preculture in 1% fructose for 18 h. Mycelial samples were taken 8 and 24 hrs after transfer, from which total RNA was isolated using TriZol (Life technologies) according to the manufacturers instructions and analysed by Northern blot analysis (Sambrook et al., 1989). Xylanase B expression levels were strongly increased in these transformants in comparison to the recipient strain, as detected after hybridisation using the radiolabelled 1 kb EcoRI/XhoI fragment of *A. niger* xlnB (Kinoshita et al., 1995).

REFERENCES

Aviv, H. and Leder, P. (1972) *Proc. Natl. Acad. Sci. USA* 11: 1408–1412.
Balance D. J. and Turner G. C. (1985) *Gene* 36: 321–331.
Dekker, R. F. H. (1983) *Biotechnol. Bioeng*. 3, 1127–1146.
Flipphi, M. J. A., Visser, J., van der Veen, P. and De Graaff, L. H. (1994) *Microbiology* 140: 2673–2682.
Garcia-Campayo and Wood (1993) *Carbohydrate Res*. 242, 229–245.
De Graaff L. H., Van den Broeck, H. C., Van Ooijen A. J. J. and Visser, J. (1994) *Mol. Microbiol*. 12: 479–490.
Harrsen, J. A. M., Kusters-van Someren, M. A., Visser, J. (1990) *Curr. Genet*. 18: 161–166.
Hombergh van den, J. P. T. W., van de Vondervoort, P. J. I., van der Heijden, N. C. B. A., and Visser, J. (1995) *Curr. Genet*. 28:299–308.
Johnstone, I. L., Hughes, S. G., Clutterbuck A. J. (1985) *EMBO J*. 4: 1307–1311.
Kinoshita K., Takano, M., Koseki, T., Ito. and Iwano, K. (1995). J. of Ferment. and Bioeng.:79, no 5, 422–428.
Kormelink, F., Searle-Van Leeuwen, M. J. F., Wood, T. M. and Voragen, A. G. J. (1993) *J. Biotechnol*. 27, 249–265.
Maniatis, T., Fritsch, E. F. and Sambrook, J. (1982) *Molecular Cloning: A Laboratory Manual*. Cold Spring Habor, N.Y.: Cold Spring Harbor Laboratory Press.
Poutanen and Puls *Appl. Microbiol. and Biotechnol*. (1988) 28, 425–432.
Rodionova, N. A., Tavobilov, I. M. and Bezborodov, A. M. *J. Appl. Biochem*. 5, 300–312 (1983)
Sambrook, J., Fritsch, E. F. and Maniatis T. (1989) *Molecular Cloning: A Laboratory Manual*. 2nd edn. Cold Spring Habor, N.Y.: Cold Spring Harbor Laboratory Press.
Sanger, F., Nickelsen, S. and Coulson A. R. (1977) *Proc. Natl. Acad. Sci. USA* 74: 5463–5467.
Schutte, J. B. (1991), Nutritional value and physiological effects of D-xylose and L-arabinose in poultry and pigs. *Datapress & Datavisions*, Wageningen, 173 pp.
Upshall, A., Gilbert, T., Saari G., O'Hara, P. J., Weglenski, P., Berse, B., Miller, K. and Timberlake, W. E. (1986) *Mol. Gen. Genet*. 204: 349–354.
Utt, E. A., Eddy, C. K., HEshav, K. F. and Ingram, L. O. (1991) *Appl. Environm. Microbiol*. 1227–1234.
Vishniac, W. and Santer, M. (1957) *Bacteriol. Rev*. 21: 195–213.
Whittington, H., Kerry-Williams, S., Bidgood, K., Dodsworth, N., Peberdy., J., Dobson, M., Hinchcliffe, E., and Ballance, D. J. (1990). *Curr. genet*. 18: 531–536.
Young, R. A. and Davies, R. W. (1983) *Science* 222: 778.

What is claimed is:

1. Recombinant cell derived from a host cell having a β-xylosidase gene, wherein said recombinant cell comprises a β-xylosidase gene that has been disrupted by a mutation in a nucleotide sequence of said β-xylosidase gene, said β-xylosidase gene prior to disruption encoding a peptide having β-xylosidase activity, said peptide comprising at least 60% amino acid identity in the primary sequence with the amino acid sequence of SEQ ID NO: 3.

2. Recombinant cell derived from a host cell having a β-xylosidase gene, wherein said recombinant cell comprises a β-xylosidase gene that has been disrupted by a mutation in a nucleotide sequence of said β-xylosidase gene, said nucleotide sequence hybridizing under stringent conditions with a nucleotide sequence of SEQ ID NO: 1.

3. A method for the production of a xylanolytic enzyme preparation, which is essentially free of β-xylosidase activity, comprising culturing said recombinant cell according to claim 1 and obtaining enzymes from the culture medium.

4. Method according to claim 3 wherein the preparation is an endoxylanase-containing preparation.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 4108 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Aspergillus niger (CBS 120.49)
    (B) STRAIN: NW147

(ix) FEATURE:
    (A) NAME/KEY: TATA_signal
    (B) LOCATION: 787..794

(ix) FEATURE:
    (A) NAME/KEY: CDS
    (B) LOCATION: 855..3266
    (D) OTHER INFORMATION: /EC_number= 3.2.1.37
        /product= "1,4-beta-D-xylan xylanohydrolase"
        /gene= "xlnD"
        /standard_name= "beta-xylosidase"

(ix) FEATURE:
    (A) NAME/KEY: sig_peptide
    (B) LOCATION: 855..932

(ix) FEATURE:
    (A) NAME/KEY: mat_peptide
    (B) LOCATION: 933..3266

(ix) FEATURE:
    (A) NAME/KEY: polyA_site
    (B) LOCATION: 3383

(ix) FEATURE:
    (A) NAME/KEY: polyA_site
    (B) LOCATION: 3404

(xi) SEQUENCE DESCRIPTION: SEQ ID NO: 1:

```
CTGCAGGCCA TGTATCCTGC GAAGATGGGT GAGTGGAAGA AAATCGTCAA GATTGAGGCG      60

GAGATGGCGA GGGCCGCGAT GAAGAAGGGT GGCTGGGCAC CGGAGAAGCC AGCCACCGCC     120

ACGGCGGCGC AGATGAGTAT ACCGTATGCG GTGGCGTTGC AGGTTCTGGA TGGGGAGATT     180

GTGCCGGGGC AGTTTGCGCC GGGCATGTTG AATCGGGAGG AGTTATGGGA TGTGATTAGG     240

CTGGTGGAAT GTCGGGAGGC CAAGGAGCTG GATAATACGT GGGCGCAGAG GGTCAAGATC     300

ACGTTTGAGG ATGGGGAGGT GGTGGAGAAG TTGTTGAAGG CTCCGAAGGG AGTCCATCCT     360

GGGGTGACGA ATGAGGAGGT GTTGCAGAAG TGGCGGGCTG TGACGAAGGG GGTAATTTCG     420

GAAGAGAGGC AGAAGAAGAT CGAGGAGATT GTGTTGAATT TGGAAGAGGT GGAGGATGTG     480

GCTGGTGTTT TGGGCGAGTT GTTGAGGGAA GAGACGGTGA ATGTGCTGCA GTAGACGGTT     540

ACCCCATTTG GACGGGGATG GCTTCATATT TCCCAAGCGA TGTCACGCCA TAGAAAGGGC     600

ACATTTACCC GGTGCCTGAG CGAAACTCTA CTTCGAAGAC AATGCCAATG TTTAACTATC     660

TTGTTTTAAT TGCTAAATGC AAACATTCCA GGTTCTTCCT AATGCCGGCT AAATCATTCA     720

GGCTAAACCC CCGCGATGAA GTCAATCGGT CATTCTCCGG CGCATCTCCG CATCTCCGCA     780

AACCGCTATA AAATCTACCC CAGATTCAGT CCCCGGCCAC CTTTCTATCC CCCCCCCAC      840
```

AGACTGGCTC AACC ATG GCG CAC TCA ATG TCT CGT CCC GTG GCT GCC ACT     890
            Met Ala His Ser Met Ser Arg Pro Val Ala Ala Thr
            -26 -25               -20                    -15

GCC GCT GCT CTG CTG GCT CTG GCT CTT CCT CAA GCT CTT GCC CAG GCC     938
Ala Ala Ala Leu Leu Ala Leu Ala Leu Pro Gln Ala Leu Ala Gln Ala
        -10                 -5                     1

AAC ACC AGC TAC GTC GAC TAC AAC ATC GAA GCC AAC CCG GAC TTG TAT     986
Asn Thr Ser Tyr Val Asp Tyr Asn Ile Glu Ala Asn Pro Asp Leu Tyr
         5                 10                 15

```
CCT TTG TGC ATA GAA ACC ATC CCA CTG AGC TTC CCC GAC TGC CAG AAT     1034
Pro Leu Cys Ile Glu Thr Ile Pro Leu Ser Phe Pro Asp Cys Gln Asn
 20                  25                  30

GGT CCC CTG CGC AGC CAT CTC ATC TGT GAT GAA ACA GCC ACC CCC TAT     1082
Gly Pro Leu Arg Ser His Leu Ile Cys Asp Glu Thr Ala Thr Pro Tyr
 35                  40                  45                  50

GAC CGA GCA GCA TCG CTC ATC TCG CTC TTC ACC CTG GAC GAG CTG ATC     1130
Asp Arg Ala Ala Ser Leu Ile Ser Leu Phe Thr Leu Asp Glu Leu Ile
             55                  60                  65

GCC AAC ACC GGC AAC ACC GGC CTC GGT GTC TCC CGA CTG GGC CTC CCT     1178
Ala Asn Thr Gly Asn Thr Gly Leu Gly Val Ser Arg Leu Gly Leu Pro
             70                  75                  80

GCA TAC CAA GTA TGG AGT GAA GCT CTT CAC GGC CTC GAC CGT GCC AAT     1226
Ala Tyr Gln Val Trp Ser Glu Ala Leu His Gly Leu Asp Arg Ala Asn
             85                  90                  95

TTC AGC GAC TCA GGA GCC TAC AAT TGG GCC ACC TCA TTC CCC CAG CCC     1274
Phe Ser Asp Ser Gly Ala Tyr Asn Trp Ala Thr Ser Phe Pro Gln Pro
100                 105                 110

ATC CTG ACC ACC GCG GCC CTC AAC CGC ACC CTC ATC CAC CAA ATC GCC     1322
Ile Leu Thr Thr Ala Ala Leu Asn Arg Thr Leu Ile His Gln Ile Ala
115                 120                 125                 130

TCC ATC ATC TCT ACC CAA GGC CGC GCC TTC AAC AAC GCC GGC CGC TAC     1370
Ser Ile Ile Ser Thr Gln Gly Arg Ala Phe Asn Asn Ala Gly Arg Tyr
                135                 140                 145

GGC CTC GAC GTC TAC GCC CCC AAC ATC AAC ACC TTC CGC CAC CCC GTC     1418
Gly Leu Asp Val Tyr Ala Pro Asn Ile Asn Thr Phe Arg His Pro Val
                150                 155                 160

TGG GGT CGC GGA CAA GAA ACC CCA GGA GAG GAC GTC TCT CTC GCC GCC     1466
Trp Gly Arg Gly Gln Glu Thr Pro Gly Glu Asp Val Ser Leu Ala Ala
                165                 170                 175

GTC TAC GCC TAC GAA TAC ATC ACC GGC ATC CAG GGT CCC GAC CCA GAA     1514
Val Tyr Ala Tyr Glu Tyr Ile Thr Gly Ile Gln Gly Pro Asp Pro Glu
180                 185                 190

TCA AAC CTC AAA CTC GCC GCC ACG GCC AAG CAC TAC GCC GGC TAT GAC     1562
Ser Asn Leu Lys Leu Ala Ala Thr Ala Lys His Tyr Ala Gly Tyr Asp
195                 200                 205                 210

ATC GAG AAC TGG CAC AAC CAC TCC CGC CTG GGC AAC GAC ATG AAC ATC     1610
Ile Glu Asn Trp His Asn His Ser Arg Leu Gly Asn Asp Met Asn Ile
                215                 220                 225

ACC CAG CAA GAC CTC TCC GAA TAC TAC ACG CCC CAA TTC CAC GTC GCC     1658
Thr Gln Gln Asp Leu Ser Glu Tyr Tyr Thr Pro Gln Phe His Val Ala
                230                 235                 240

GCC CGC GAC GCC AAA GTC CAG AGT GTC ATG TGC GCC TAC AAC GCC GTC     1706
Ala Arg Asp Ala Lys Val Gln Ser Val Met Cys Ala Tyr Asn Ala Val
                245                 250                 255

AAC GGC GTC CCT GCC TGC GCC GAC TCC TAC TTC CTC CAG ACC CTC CTC     1754
Asn Gly Val Pro Ala Cys Ala Asp Ser Tyr Phe Leu Gln Thr Leu Leu
260                 265                 270

CGC GAC ACC TTC GGA TTT GTC GAC CAC GGA TAC GTC TCC AGC GAC TGC     1802
Arg Asp Thr Phe Gly Phe Val Asp His Gly Tyr Val Ser Ser Asp Cys
275                 280                 285                 290

GAT GCC GCC TAT AAC ATC TAC AAC CCC CAC GGC TAT GCC TCC TCC CAG     1850
Asp Ala Ala Tyr Asn Ile Tyr Asn Pro His Gly Tyr Ala Ser Ser Gln
                295                 300                 305

GCT GCC GCT GCC GCT GAG GCC ATC CTC GCC GGC ACC GAC ATC GAC TGC     1898
Ala Ala Ala Ala Ala Glu Ala Ile Leu Ala Gly Thr Asp Ile Asp Cys
                310                 315                 320

GGT ACC ACC TAC CAA TGG CAC CTG AAC GAG TCC ATC GCT GCG GGA GAT     1946
Gly Thr Thr Tyr Gln Trp His Leu Asn Glu Ser Ile Ala Ala Gly Asp
                325                 330                 335
```

```
CTC TCT CGC GAT GAT ATT GAG CAG GGT GTG ATT CGT CTC TAC ACG ACC        1994
Leu Ser Arg Asp Asp Ile Glu Gln Gly Val Ile Arg Leu Tyr Thr Thr
    340             345                 350

CTC GTG CAG GCC GGA TAC TTC GAC TCC AAC ACC ACA AAG GCG AAC AAC        2042
Leu Val Gln Ala Gly Tyr Phe Asp Ser Asn Thr Thr Lys Ala Asn Asn
355             360                 365                     370

CCC TAC CGC GAC CTC TCC TGG TCC GAC GTC CTT GAG ACG GAC GCA TGG        2090
Pro Tyr Arg Asp Leu Ser Trp Ser Asp Val Leu Glu Thr Asp Ala Trp
                375                 380                 385

AAC ATC TCC TAC CAA GCC GCG ACG CAG GGC ATT GTC CTT CTC AAG AAC        2138
Asn Ile Ser Tyr Gln Ala Ala Thr Gln Gly Ile Val Leu Leu Lys Asn
            390                 395                 400

TCC AAC AAC GTC CTC CCC CTC ACC GAG AAA GCT TAC CCA CCA TCC AAC        2186
Ser Asn Asn Val Leu Pro Leu Thr Glu Lys Ala Tyr Pro Pro Ser Asn
        405                 410                 415

ACC ACC GTC GCC CTC ATC GGT CCC TGG GCC AAC GCC ACC ACC CAA CTC        2234
Thr Thr Val Ala Leu Ile Gly Pro Trp Ala Asn Ala Thr Thr Gln Leu
    420                 425                 430

CTG GGC AAC TAC TAC GGC AAC GCT CCC TAC ATG ATC AGC CCC CGC GCC        2282
Leu Gly Asn Tyr Tyr Gly Asn Ala Pro Tyr Met Ile Ser Pro Arg Ala
435             440                 445                 450

GCC TTC GAA GAA GCC GGA TAC AAA GTC AAC TTC GCC GAG GGC ACC GGT        2330
Ala Phe Glu Glu Ala Gly Tyr Lys Val Asn Phe Ala Glu Gly Thr Gly
                455                 460                 465

ATC TCC TCC ACA AGC ACC TCG GGC TTC GCT GCC GCC TTA TCC GCC GCA        2378
Ile Ser Ser Thr Ser Thr Ser Gly Phe Ala Ala Ala Leu Ser Ala Ala
            470                 475                 480

CAA TCC GCC GAC GTG ATA ATC TAC GCC GGT GGT ATC GAC AAT ACC CTT        2426
Gln Ser Ala Asp Val Ile Ile Tyr Ala Gly Gly Ile Asp Asn Thr Leu
        485                 490                 495

GAA GCG GAG GCA CTG GAT CGA GAG AGT ATC GCG TGG CCG GGT AAC CAA        2474
Glu Ala Glu Ala Leu Asp Arg Glu Ser Ile Ala Trp Pro Gly Asn Gln
    500                 505                 510

CTG GAC TTG ATC CAG AAG CTC GCC TCG GCG GCC GGA AAG AAG CCG CTC        2522
Leu Asp Leu Ile Gln Lys Leu Ala Ser Ala Ala Gly Lys Lys Pro Leu
515             520                 525                 530

ATC GTC CTC CAA ATG GGC GGC GGA CAG GTC GAT TCC TCT TCG CTC AAG        2570
Ile Val Leu Gln Met Gly Gly Gly Gln Val Asp Ser Ser Ser Leu Lys
                535                 540                 545

AAC AAC ACC AAT GTT TCT GCA CTT CTC TGG GGC GGA TAC CCC GGC CAA        2618
Asn Asn Thr Asn Val Ser Ala Leu Leu Trp Gly Gly Tyr Pro Gly Gln
            550                 555                 560

TCT GGC GGC TTC GCT TTG CGG GAT ATC ATC ACG GGG AAG AAG AAC CCC        2666
Ser Gly Gly Phe Ala Leu Arg Asp Ile Ile Thr Gly Lys Lys Asn Pro
        565                 570                 575

GCG GGT AGA CTA GTC ACG ACG CAG TAC CCT GCC AGC TAC GCG GAG GAG        2714
Ala Gly Arg Leu Val Thr Thr Gln Tyr Pro Ala Ser Tyr Ala Glu Glu
    580                 585                 590

TTC CCG GCG ACA GAT ATG AAC CTT CGT CCT GAG GGT GAT AAC CCT GGT        2762
Phe Pro Ala Thr Asp Met Asn Leu Arg Pro Glu Gly Asp Asn Pro Gly
595             600                 605                 610

CAG ACG TAT AAA TGG TAC ACC GGC GAA GCC GTG TAC GAG TTC GGC CAC        2810
Gln Thr Tyr Lys Trp Tyr Thr Gly Glu Ala Val Tyr Glu Phe Gly His
                615                 620                 625

GGG TTA TTC TAC ACG ACC TTC GCG GAA TCC TCC AGC AAT ACC ACT ACA        2858
Gly Leu Phe Tyr Thr Thr Phe Ala Glu Ser Ser Ser Asn Thr Thr Thr
            630                 635                 640

AAG GAA GTT AAG CTC AAC ATC CAG GAC ATT CTT TCC CAG ACA CAC GAA        2906
Lys Glu Val Lys Leu Asn Ile Gln Asp Ile Leu Ser Gln Thr His Glu
```

-continued

```
           645                   650                   655
GAC CTG GCG TCG ATT ACC CAG CTC CCT GTG CTG AAC TTC ACC GCC AAT        2954
Asp Leu Ala Ser Ile Thr Gln Leu Pro Val Leu Asn Phe Thr Ala Asn
        660                   665                   670

ATC AGG AAC ACT GGA AAG CTG GAA TCG GAT TAC ACC GCT ATG GTA TTC        3002
Ile Arg Asn Thr Gly Lys Leu Glu Ser Asp Tyr Thr Ala Met Val Phe
675                   680                   685                   690

GCC AAT ACC TCT GAT GCC GGG CCG GCG CCG TAT CCC AAG AAG TGG CTG        3050
Ala Asn Thr Ser Asp Ala Gly Pro Ala Pro Tyr Pro Lys Lys Trp Leu
                695                   700                   705

GTC GGG TGG GAT CGG CTT GGG GAG GTG AAG GTC GGG GAG ACG AGG GAG        3098
Val Gly Trp Asp Arg Leu Gly Glu Val Lys Val Gly Glu Thr Arg Glu
            710                   715                   720

TTG AGG GTC CCC GTT GAG GTG GGG AGC TTT GCG AGG GTG AAT GAG GAT        3146
Leu Arg Val Pro Val Glu Val Gly Ser Phe Ala Arg Val Asn Glu Asp
        725                   730                   735

GGC GAT TGG GTG GTG TTT CCG GGA ACG TTT GAG TTG GCG TTG AAT TTG        3194
Gly Asp Trp Val Val Phe Pro Gly Thr Phe Glu Leu Ala Leu Asn Leu
    740                   745                   750

GAG AGG AAG GTT CGG GTG AAG GTT GTT CTT GAG GGT GAG GAG GAA GTC        3242
Glu Arg Lys Val Arg Val Lys Val Val Leu Glu Gly Glu Glu Glu Val
755                   760                   765                   770

GTG CTG AAG TGG CCG GGG AAG GAG TAGAAAATAC TATTCTGTTG ATGGCTCTAG       3296
Val Leu Lys Trp Pro Gly Lys Glu
                775

GGGATGAGAG TCAGCCTATT ACTGGATATG CATAGTGGTG ATACGATGTA TATAGCTCTA      3356

TGAAGTAATT AGTTCAAGTG GGAATACCCC TTTCACACAT ATAGTATGCT GTTATTCCGA      3416

AATAGGGATC ATTTCTGATT AATAGTAGCG GTAGCGATGG TCACACACGA CTTAATGTTC      3476

CCCATTGTAC CGGAAGTAAC AATTCCAGTG ACCTCTTAGA AGAAAGACAG CAAGAAAAAG      3536

TAAGAAAGGG AAATTGATCA AAAAATAAGG CCATCTACAG CCTATTCACA TTTAGCCGGA      3596

TCTGCAATAC AGCTACAGAA ATAAAGTTTG TTAGGCTGCT TGCTAGCATA GCTCCTACTA      3656

TACTAAACCA ACACAATGGG ACAATACCCC AATTAACCAG CCCTCACTCA ACACAAGTGA      3716

ATCCTACCGA CAACATGCAT AAACCACTGC TTCCCCACCC AGCACCCTTC TTCACGATCA      3776

GATCACGGAG AATTACCAAC TACTCTTCGC ATAAAACGTA AACAACGGCC TCGGGCCAGG      3836

ATCCGTCCGA CTCAAAAGCA ACAAATCCCT CGTTCGCATA CTAGCCACAT GAACCTGTTG      3896

CTCCGAGACC TCCTCAACTG GGTCTTCAAA TGCCCAGAAG ACGCTTTCTT CTCGATATCC      3956

ATCGGATACT CGCTGGCCGC TTAGACATAT GAACGATGAG TCTCGTCTGC CAAAGGAAAC      4016

AACCGTGTTC CCGAATCCAG TGTCAAAGTC GTAGGTCTGG AATTTGAAAA GTGTTCGGGC      4076

GTTTCCTTGG AGGGTCGGGA GTGCGACTGC AG                                    4108
```

(2) INFORMATION FOR SEQ ID NO: 2:

(i) SEQUENCE CHARACTERISTICS:
        (A) LENGTH: 4173 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Aspergillus niger -continued

```
        (B) STRAIN: CBS 120.49
        (C) INDIVIDUAL ISOLATE: N400

(ix) FEATURE:
        (A) NAME/KEY: CDS
        (B) LOCATION: join(948..1173, 1238..3495, 3550..3690)
        (C) IDENTIFICATION METHOD: experimental
        (D) OTHER INFORMATION: /function= "Transcriptional
            activator of xylanolytic genes"
            /product= "Binuclear Zn finger DNA binding
            protein"
            /gene= "xlnR"
            /standard_name= "XYL R"

(ix) FEATURE:
        (A) NAME/KEY: exon
        (B) LOCATION: 948..1173

(ix) FEATURE:
        (A) NAME/KEY: intron
        (B) LOCATION: 1174..1237

(ix) FEATURE:
        (A) NAME/KEY: exon
        (B) LOCATION: 1238..3495

(ix) FEATURE:
        (A) NAME/KEY: intron
        (B) LOCATION: 3496..3549

(ix) FEATURE:
        (A) NAME/KEY: exon
        (B) LOCATION: 3550..3690

(xi) SEQUENCE DESCRIPTION: SEQ ID NO: 2:
```

```
CCCGGGCTTG GTTGGTCTCC GTCTGGCTTC CCCGCCTTTT TCCCCTGCAA TTCTGCATCC        60

CCAATCCTTC TTTTTTCTTT GCCTCGCCAG GCTGTGTCTT TTTTCCCCCT CCCCCTCCTC       120

CCTCGTCAGC TTCTCTTCGA CAGCATGCGT GAGGGTCTGC TACCAACTAC AATCCTTGTT       180

CTCACTGTCT GATGGTCTGA CCCGACCGTG GTGTCTGTGG TGTGTGTGTG AGAGAGAAAG       240

GAAAGCTAGT CAGTCCAGTC ACTCTTTCTC GTGGGTTCTT CACCTTCCCC GGACCTGCCC       300

TCCGACACTA AAAAGCCACT TCCCCCCAAC TGGTTAGTTG CTGCTAGTCT CCTTAGTTCA       360

TGGTCGGCCT TGTCGCTTCT CCGGCTGACA TTCTCCTCTT CTGCTGCCTT CTAGGTCCCT       420

GTTTTTTAGT CCCTGTTTTA GTTGCCCCGC AGACTGAATC GGCAATGCCG TGGAGTTGAT       480

CGTTCCGTGG TTTCCTTGCG ACCGCTCCTC TGCTTCATCA TCTTTTTCCT CCTGCCCTCC       540

TGGTCTTGAA TCGCCTGGCC CTCGTCTAGG ATCGTTGCG CCAGTGTCGC CTTAATCTCC        600

TTTCCCGCTA GCGTAGTGCC CTTTCACGCT TGGGGCCTTA CGGCCCTTCC ATTCGCCAGC       660

GGTCTGAATA CCTCACTTTC CCCCCAACG ACCGGGGTCT TCATGACCCG CTGGGGTGAT        720

TGTTCCGCCC GGTGAGGATG TCAACCCCCT CGATTCCTCA ATTCACCAGT CCTTTCTCTC       780

CCTTCTCTTC CGGATCGCAC TCGACTGGCA TGGCGCCGTC TCAGACTGTC GGGTTGGATA       840

CGCTCGCCGA GGGCTCGCAG TACGTCCTGG AACAATTGCA GCTGTCGCGA GACGCTGCGG       900

GAACCGGTGC CGGCGATGGC GCGACCTCCA CTTCCTTGCG AAATTCC ATG TCG CAT         956
                                                 Met Ser His
                                                  1

ACG AAG GAT CAA CCA CCC TTT GAT AAT GAG AAG AAC CAG AGC ACT GGC        1004
Thr Lys Asp Gln Pro Pro Phe Asp Asn Glu Lys Asn Gln Ser Thr Gly
      5                  10                  15

TCG GGT TTT AGG GAC GCT CTG CAA AGA GAT CCC CTC GTG GAG GCT CGC        1052
Ser Gly Phe Arg Asp Ala Leu Gln Arg Asp Pro Leu Val Glu Ala Arg
 20                  25                  30                  35

TCT GCC GTC CGC AAA ACC TCG TCT TCA GCT CCG GTT CGC CGC CGA ATC        1100
```

```
                                                         -continued

Ser Ala Val Arg Lys Thr Ser Ser Ala Pro Val Arg Arg Ile
                40              45                50

AGC CGT GCG TGT GAC CAG TGT AAC CAA CTC CGA ACG AAA TGC GAC GGG      1148
Ser Arg Ala Cys Asp Gln Cys Asn Gln Leu Arg Thr Lys Cys Asp Gly
            55                  60                  65

CAG CAT CCG TGC GCT CAT TGC ATT   G GTAGGCTTCC GCTCTTTCTC             1193
Gln His Pro Cys Ala His Cys Ile
        70              75

CGATGCCGGC GATGAGGCGG ACGCTTGACT GACCTGTTCT GTAG  AA TTC GGA CTG     1248
                                                  Glu Phe Gly Leu

ACC TGC GAG TAT GCG CGA GAA CGC AAG AAG CGT GGA AAA GCG TCG AAG      1296
Thr Cys Glu Tyr Ala Arg Glu Arg Lys Lys Arg Gly Lys Ala Ser Lys
 80              85                  90                  95

AAG GAT CTG GCG GCG GCA GCT GCG GCG GCT ACC CAA GGG TCG AAT GGT      1344
Lys Asp Leu Ala Ala Ala Ala Ala Ala Ala Thr Gln Gly Ser Asn Gly
                100                 105                 110

CAT TCC GGG CAG GCC AAC GCG TCG CTA ATG GGC GAG CGA ACG TCG GAA      1392
His Ser Gly Gln Ala Asn Ala Ser Leu Met Gly Glu Arg Thr Ser Glu
            115                 120                 125

GAC AGC CGG CCA GGA CAA GAC GTG AAC GGC ACA TAC GAC TCG GCT TTT      1440
Asp Ser Arg Pro Gly Gln Asp Val Asn Gly Thr Tyr Asp Ser Ala Phe
        130                 135                 140

GAG AGC CAC CAT CTT AGC TCG CAG CCA TCG CAT ATG CAG CAT GCA AGC      1488
Glu Ser His His Leu Ser Ser Gln Pro Ser His Met Gln His Ala Ser
145                 150                 155

ACT GCA GGG ATA TCC GGC CTG CAC GAG TCT CAG ACG GCA CCG TCG CAT      1536
Thr Ala Gly Ile Ser Gly Leu His Glu Ser Gln Thr Ala Pro Ser His
160                 165                 170                 175

TCG CAA TCA TCG CTA GGA ACG ACT ATC GAT GCG ATG CAT TTG AAT CAT      1584
Ser Gln Ser Ser Leu Gly Thr Thr Ile Asp Ala Met His Leu Asn His
            180                 185                 190

TTC AAC ACG ATG AAC GAT TCC GGT CGC CCG GCA ATG TCC ATA TCC GAT      1632
Phe Asn Thr Met Asn Asp Ser Gly Arg Pro Ala Met Ser Ile Ser Asp
        195                 200                 205

CTG CGT TCG CTA CCC CCG TCC GTC TTA CCA CCG CAA GGA CTA AGC TCC      1680
Leu Arg Ser Leu Pro Pro Ser Val Leu Pro Pro Gln Gly Leu Ser Ser
    210                 215                 220

GGG TAC AAC GCG AGC GCC TTC GCT TTG GTG AAC CCG CAA GAG CCG GGC      1728
Gly Tyr Asn Ala Ser Ala Phe Ala Leu Val Asn Pro Gln Glu Pro Gly
225                 230                 235

TCA CCA GCT AAC CAG TTT CGC TTG GGA AGC TCA GCG GAA AAC CCA ACC      1776
Ser Pro Ala Asn Gln Phe Arg Leu Gly Ser Ser Ala Glu Asn Pro Thr
240                 245                 250                 255

GCA CCG TTT CTT GGT CTC TCG CCT CCA GGA CAG TCG CCT GGA TGG CTC      1824
Ala Pro Phe Leu Gly Leu Ser Pro Pro Gly Gln Ser Pro Gly Trp Leu
            260                 265                 270

CCT CTT CCC TCG CCA TCT CCT GCC AAC TTT CCT TCT TTC AGC TTG CAT      1872
Pro Leu Pro Ser Pro Ser Pro Ala Asn Phe Pro Ser Phe Ser Leu His
        275                 280                 285

CCG TTT TCC AGC ACT TTA CGA TAC CCT GTT TTG CAG CCG GTC CTG CCT      1920
Pro Phe Ser Ser Thr Leu Arg Tyr Pro Val Leu Gln Pro Val Leu Pro
    290                 295                 300

CAC ATC GCC TCC ATT ATT CCG CAG TCG CTA GCG TGT GAC CTT CTG GAT      1968
His Ile Ala Ser Ile Ile Pro Gln Ser Leu Ala Cys Asp Leu Leu Asp
305                 310                 315

GTT TAC TTC ACT AGT TCC TCT TCG TCC CAC CTG TCT CCC TTG TCC CCA      2016
Val Tyr Phe Thr Ser Ser Ser Ser His Leu Ser Pro Leu Ser Pro
320                 325                 330                 335

TAC GTG GTG GGC TAC ATC TTC CGC AAG CAG TCT TTC CTT CAC CCG ACA      2064
```

```
                                        -continued

Tyr Val Val Gly Tyr Ile Phe Arg Lys Gln Ser Phe Leu His Pro Thr
                340                 345                 350

AAA CCC CGA ATA TGC AGC CCC GGT CTC CTG GCG AGT ATG CTC TGG GTA      2112
Lys Pro Arg Ile Cys Ser Pro Gly Leu Leu Ala Ser Met Leu Trp Val
            355                 360                 365

GCC GCA CAA ACG AGT GAA GCT GCG TTT CTG ACA TCG CCG CCC TCG GCT      2160
Ala Ala Gln Thr Ser Glu Ala Ala Phe Leu Thr Ser Pro Pro Ser Ala
                370                 375                 380

CGG GGG CGT GTA TGC CAG AAA CTG CTA GAA CTG ACC ATT GGT TTG CTC      2208
Arg Gly Arg Val Cys Gln Lys Leu Leu Glu Leu Thr Ile Gly Leu Leu
385                 390                 395

CGA CCG TTG GTC CAT GGT CCT GCT ACC GGA GAA GCG TCG CCC AAC TAT      2256
Arg Pro Leu Val His Gly Pro Ala Thr Gly Glu Ala Ser Pro Asn Tyr
400                 405                 410                 415

GCG GCG AAT ATG GTC ATC AAT GGC GTC GCT CTG GGC GGA TTT GGG GTC      2304
Ala Ala Asn Met Val Ile Asn Gly Val Ala Leu Gly Gly Phe Gly Val
                420                 425                 430

TCC ATG GAT CAG CTG GGC GCG CAA AGT AGC GCC ACC GGC GCC GTG GAT      2352
Ser Met Asp Gln Leu Gly Ala Gln Ser Ser Ala Thr Gly Ala Val Asp
                435                 440                 445

GAT GTA GCA ACT TAT GTG CAT CTT GCG ACA GTA GTA TCC GCC AGC GAG      2400
Asp Val Ala Thr Tyr Val His Leu Ala Thr Val Val Ser Ala Ser Glu
                450                 455                 460

TAC AAG GCG GCC AGC ATG CGC TGG TGG ACT GCG GCG TGG TCT CTA GCG      2448
Tyr Lys Ala Ala Ser Met Arg Trp Trp Thr Ala Ala Trp Ser Leu Ala
465                 470                 475

CGT GAG CTG AAG CTA GGC CGT GAG CTG CCA CCC AAT GTT TCC CAC GCA      2496
Arg Glu Leu Lys Leu Gly Arg Glu Leu Pro Pro Asn Val Ser His Ala
480                 485                 490                 495

CGG CAA GAT GGA GAG CGA GAT GGG GAT GGC GAG GCG GAC AAA CGA CAT      2544
Arg Gln Asp Gly Glu Arg Asp Gly Asp Gly Glu Ala Asp Lys Arg His
                500                 505                 510

CCT CCG ACC CTC ATC ACG TCA CTG GGT CAT GGA TCG GGA AGC TCC GGC      2592
Pro Pro Thr Leu Ile Thr Ser Leu Gly His Gly Ser Gly Ser Ser Gly
                515                 520                 525

ATT AAT GTC ACC GAA GAG GAG CGT GAG GAG CGT CGA CGC CTA TGG TGG      2640
Ile Asn Val Thr Glu Glu Glu Arg Glu Glu Arg Arg Arg Leu Trp Trp
                530                 535                 540

CTC TTA TAT GCG ACC GAT CGG CAC CTG GCG CTG TGC TAC AAC CGG CCC      2688
Leu Leu Tyr Ala Thr Asp Arg His Leu Ala Leu Cys Tyr Asn Arg Pro
    545                 550                 555

CTC ACG CTG CTG GAC AAG GAA TGT GGC GGG CTG CTG CAG CCG ATG AAC      2736
Leu Thr Leu Leu Asp Lys Glu Cys Gly Gly Leu Leu Gln Pro Met Asn
560                 565                 570                 575

GAT GAT CTG TGG CAG GTC GGC GAC TTT GCA GCG GCT GCC TAC CGC CAG      2784
Asp Asp Leu Trp Gln Val Gly Asp Phe Ala Ala Ala Ala Tyr Arg Gln
                580                 585                 590

GTC GGA CCG CCC GTC GAG TGT ACG GGT CAC AGC ATG TAT GGA TAC TTT      2832
Val Gly Pro Pro Val Glu Cys Thr Gly His Ser Met Tyr Gly Tyr Phe
                595                 600                 605

CTA CCG CTG ATG ACG ATT CTT GGA GGG ATC GTC GAT CTG CAC CAC GCT      2880
Leu Pro Leu Met Thr Ile Leu Gly Gly Ile Val Asp Leu His His Ala
            610                 615                 620

GAG AAT CAT CCG CGC TTT GGC CTG GCG TTC CGC AAT AGC CCG GAG TGG      2928
Glu Asn His Pro Arg Phe Gly Leu Ala Phe Arg Asn Ser Pro Glu Trp
625                 630                 635

GAG CGT CAG GTA CTG GAC GTT ACG CGG CAG CTG GAC ACA TAT GGG CGC      2976
Glu Arg Gln Val Leu Asp Val Thr Arg Gln Leu Asp Thr Tyr Gly Arg
640                 645                 650                 655
```

```
AGC TTG AAG GAA TTC GAG GCC CGC TAC ACC AGC AAC TTG ACT CTG GGG      3024
Ser Leu Lys Glu Phe Glu Ala Arg Tyr Thr Ser Asn Leu Thr Leu Gly
            660                 665                 670

GCT ACG GAT AAC GAG CCT GTC GTC GAA GGT GCC CAC TTG GAT CAC ACG      3072
Ala Thr Asp Asn Glu Pro Val Val Glu Gly Ala His Leu Asp His Thr
            675                 680                 685

AGT CCT TCG GGG CGC TCC AGC AGC ACC GTG GGA TCG CGG GTG AGC GAG      3120
Ser Pro Ser Gly Arg Ser Ser Ser Thr Val Gly Ser Arg Val Ser Glu
            690                 695                 700

TCC ATC GTC CAC ACG AGG ATG GTG GTC GCC TAC GGG ACG CAT ATC ATG      3168
Ser Ile Val His Thr Arg Met Val Val Ala Tyr Gly Thr His Ile Met
        705                 710                 715

CAC GTC CTG CAT ATT TTG CTC GCG GGA AAA TGG GAC CCG GTG AAT CTG      3216
His Val Leu His Ile Leu Leu Ala Gly Lys Trp Asp Pro Val Asn Leu
720                 725                 730                 735

TTG GAA GAT CAT GAT CTG TGG ATC TCC TCG GAG TCG TTT GTC TCG GCC      3264
Leu Glu Asp His Asp Leu Trp Ile Ser Ser Glu Ser Phe Val Ser Ala
                740                 745                 750

ATG AGC CAT GCG GTC GGT GCC GCA GAA GCA GCG GCA GAA ATC TTG GAG      3312
Met Ser His Ala Val Gly Ala Ala Glu Ala Ala Ala Glu Ile Leu Glu
            755                 760                 765

TAC GAC CCG GAT CTC AGC TTC ATG CCG TTC TTC TTC GGG ATT TAC CTA      3360
Tyr Asp Pro Asp Leu Ser Phe Met Pro Phe Phe Phe Gly Ile Tyr Leu
            770                 775                 780

CTA CAG GGC AGT TTC TTG CTG CTA CTG GCG GCG GAC AAG TTG CAG GGC      3408
Leu Gln Gly Ser Phe Leu Leu Leu Ala Ala Asp Lys Leu Gln Gly
        785                 790                 795

GAT GCC AGT CCC AGT GTC GTG CGG GCA TGC GAG ACG ATC GTG CGG GCG      3456
Asp Ala Ser Pro Ser Val Val Arg Ala Cys Glu Thr Ile Val Arg Ala
800                 805                 810                 815

CAT GAA GCG TGC GTC GTG ACC TTG AAC ACG GAG TAC CAG GTAGGTTTTC      3505
His Glu Ala Cys Val Val Thr Leu Asn Thr Glu Tyr Gln
            820                 825

TTGTTTCTCT CCCTAGCTTG GCAATAGTAG CTAACACAAT GTAG AGG ACA TTC CGC    3561
                                                 Arg Thr Phe Arg
                                                         830

AAG GTC ATG CGA TCG GCG CTG GCA CAG GTT CGA GGA CGC ATC CCA GAG      3609
Lys Val Met Arg Ser Ala Leu Ala Gln Val Arg Gly Arg Ile Pro Glu
            835                 840                 845

GAC TTT GGG GAG CAG CAG CAG CGC CGA CGC GAA GTG CTT GCG CTA TAC      3657
Asp Phe Gly Glu Gln Gln Gln Arg Arg Arg Glu Val Leu Ala Leu Tyr
        850                 855                 860

CGC TGG AGC GGC GAT GGC AGT GGG CTG GCA CTG TAGTTTTGCA GTAACACGGC    3710
Arg Trp Ser Gly Asp Gly Ser Gly Leu Ala Leu
865                 870                 875

TGATGATGAG ATGCGATTTA TGGCGGTGCA TTGACCGGTC AATGGCTTCT TACATTCTGA    3770

TTTGATACTA CTTTTGGATT CGCTATTTCA CTCCGGGCTT ATGCTGGCTT CATTGTCAAG    3830

AGGGGTGGCA TGGCGAATGG AAATATGCTT ACTTCGTGTT GATACGGATT CGTACATATA    3890

CTTTGGTGAT ATATGTGGAT ATTTGTGGCA TGTACACTAT GCGTGATCTT TGGACATGAT    3950

ACTTTGATAC CAGGTCAATC TAATTGCGTT CTTTTCATTT GTTGCGCAAC AGCCGAGGTA    4010

TGACGCCATG GCTGAGATAA GCTGCCGATA AGCATTCGCA TTCCATCCTC CATCGAAGCA    4070

CCAAAATCTT CTTCATATAA CCAATCCATC AATTCAACAT TCGTAATGAC AATAGTATAA    4130

TCCCCAAAAT GCCCTCCCTA TTACACTCCC TCCGCACTTC CCC                      4173

(2) INFORMATION FOR SEQ ID NO: 3:
```

-continued

```
    (i) SEQUENCE CHARACTERISTICS:
        (A) LENGTH: 804 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Aspergillus niger (CBS 120.49)
        (B) STRAIN: NW147

(ix) FEATURE:
        (A) NAME/KEY: sig_peptide
        (B) LOCATION: 1..26

(xi) SEQUENCE DESCRIPTION: SEQ ID NO: 3:

Met Ala His Ser Met Ser Arg Pro Val Ala Thr Ala Ala Ala Leu
  1               5                  10                  15

Leu Ala Leu Ala Leu Pro Gln Ala Leu Ala Gln Ala Asn Thr Ser Tyr
                 20                  25                  30

Val Asp Tyr Asn Ile Glu Ala Asn Pro Asp Leu Tyr Pro Leu Cys Ile
             35                  40                  45

Glu Thr Ile Pro Leu Ser Phe Pro Asp Cys Gln Asn Gly Pro Leu Arg
         50                  55                  60

Ser His Leu Ile Cys Asp Glu Thr Ala Thr Pro Tyr Asp Arg Ala Ala
 65                  70                  75                  80

Ser Leu Ile Ser Leu Phe Thr Leu Asp Glu Leu Ile Ala Asn Thr Gly
                 85                  90                  95

Asn Thr Gly Leu Gly Val Ser Arg Leu Gly Leu Pro Ala Tyr Gln Val
            100                 105                 110

Trp Ser Glu Ala Leu His Gly Leu Asp Arg Ala Asn Phe Ser Asp Ser
            115                 120                 125

Gly Ala Tyr Asn Trp Ala Thr Ser Phe Pro Gln Pro Ile Leu Thr Thr
            130                 135                 140

Ala Ala Leu Asn Arg Thr Leu Ile His Gln Ile Ala Ser Ile Ile Ser
145                 150                 155                 160

Thr Gln Gly Arg Ala Phe Asn Asn Ala Gly Arg Tyr Gly Leu Asp Val
                165                 170                 175

Tyr Ala Pro Asn Ile Asn Thr Phe Arg His Pro Val Trp Gly Arg Gly
            180                 185                 190

Gln Glu Thr Pro Gly Glu Asp Val Ser Leu Ala Ala Val Tyr Ala Tyr
            195                 200                 205

Glu Tyr Ile Thr Gly Ile Gln Gly Pro Asp Pro Glu Ser Asn Leu Lys
            210                 215                 220

Leu Ala Ala Thr Ala Lys His Tyr Ala Gly Tyr Asp Ile Glu Asn Trp
225                 230                 235                 240

His Asn His Ser Arg Leu Gly Asn Asp Met Asn Ile Thr Gln Gln Asp
                245                 250                 255

Leu Ser Glu Tyr Tyr Thr Pro Gln Phe His Val Ala Ala Arg Asp Ala
            260                 265                 270

Lys Val Gln Ser Val Met Cys Ala Tyr Asn Ala Val Asn Gly Val Pro
            275                 280                 285

Ala Cys Ala Asp Ser Tyr Phe Leu Gln Thr Leu Leu Arg Asp Thr Phe
            290                 295                 300

Gly Phe Val Asp His Gly Tyr Val Ser Ser Asp Cys Asp Ala Ala Tyr
305                 310                 315                 320
```

```
Asn Ile Tyr Asn Pro His Gly Tyr Ala Ser Gln Ala Ala Ala
            325                 330             335
Ala Glu Ala Ile Leu Ala Gly Thr Asp Ile Asp Cys Gly Thr Thr Tyr
            340                 345                 350
Gln Trp His Leu Asn Glu Ser Ile Ala Ala Gly Asp Leu Ser Arg Asp
            355                 360             365
Asp Ile Glu Gln Gly Val Ile Arg Leu Tyr Thr Thr Leu Val Gln Ala
    370                 375                 380
Gly Tyr Phe Asp Ser Asn Thr Thr Lys Ala Asn Asn Pro Tyr Arg Asp
385                 390                 395                 400
Leu Ser Trp Ser Asp Val Leu Glu Thr Asp Ala Trp Asn Ile Ser Tyr
                405                 410                 415
Gln Ala Ala Thr Gln Gly Ile Val Leu Leu Lys Asn Ser Asn Asn Val
            420                 425                 430
Leu Pro Leu Thr Glu Lys Ala Tyr Pro Pro Ser Asn Thr Thr Val Ala
            435                 440                 445
Leu Ile Gly Pro Trp Ala Asn Ala Thr Thr Gln Leu Leu Gly Asn Tyr
    450                 455                 460
Tyr Gly Asn Ala Pro Tyr Met Ile Ser Pro Arg Ala Ala Phe Glu Glu
465                 470                 475                 480
Ala Gly Tyr Lys Val Asn Phe Ala Glu Gly Thr Gly Ile Ser Ser Thr
                485                 490                 495
Ser Thr Ser Gly Phe Ala Ala Ala Leu Ser Ala Ala Gln Ser Ala Asp
            500                 505                 510
Val Ile Ile Tyr Ala Gly Gly Ile Asp Asn Thr Leu Glu Ala Glu Ala
            515                 520                 525
Leu Asp Arg Glu Ser Ile Ala Trp Pro Gly Asn Gln Leu Asp Leu Ile
    530                 535                 540
Gln Lys Leu Ala Ser Ala Ala Gly Lys Lys Pro Leu Ile Val Leu Gln
545                 550                 555                 560
Met Gly Gly Gly Gln Val Asp Ser Ser Ser Leu Lys Asn Asn Thr Asn
                565                 570                 575
Val Ser Ala Leu Leu Trp Gly Gly Tyr Pro Gly Gln Ser Gly Gly Phe
            580                 585                 590
Ala Leu Arg Asp Ile Ile Thr Gly Lys Lys Asn Pro Ala Gly Arg Leu
            595                 600                 605
Val Thr Thr Gln Tyr Pro Ala Ser Tyr Ala Glu Glu Phe Pro Ala Thr
    610                 615                 620
Asp Met Asn Leu Arg Pro Glu Gly Asp Asn Pro Gly Gln Thr Tyr Lys
625                 630                 635                 640
Trp Tyr Thr Gly Glu Ala Val Tyr Glu Phe Gly His Gly Leu Phe Tyr
                645                 650                 655
Thr Thr Phe Ala Glu Ser Ser Asn Thr Thr Lys Glu Val Lys
            660                 665                 670
Leu Asn Ile Gln Asp Ile Leu Ser Gln Thr His Glu Asp Leu Ala Ser
            675                 680                 685
Ile Thr Gln Leu Pro Val Leu Asn Phe Thr Ala Asn Ile Arg Asn Thr
    690                 695                 700
Gly Lys Leu Glu Ser Asp Tyr Thr Ala Met Val Phe Ala Asn Thr Ser
705                 710                 715                 720
Asp Ala Gly Pro Ala Pro Tyr Pro Lys Lys Trp Leu Val Gly Trp Asp
                725                 730                 735
Arg Leu Gly Glu Val Lys Val Gly Glu Thr Arg Glu Leu Arg Val Pro
```

```
                    740                     745                     750
Val Glu Val Gly Ser Phe Ala Arg Val Asn Glu Asp Gly Asp Trp Val
        755                     760                     765

Val Phe Pro Gly Thr Phe Glu Leu Ala Leu Asn Leu Glu Arg Lys Val
        770                     775                     780

Arg Val Lys Val Val Leu Glu Gly Glu Glu Glu Val Val Leu Lys Trp
785                     790                     795                     800

Pro Gly Lys Glu
```